(12) United States Patent
Hashimoto et al.

(10) Patent No.: US 7,309,127 B2
(45) Date of Patent: Dec. 18, 2007

(54) OPHTHALMIC MEASURING APPARATUS

(75) Inventors: Hiroaki Hashimoto, Tokyo (JP); Yoko Hirohara, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 609 days.

(21) Appl. No.: 10/633,408

(22) Filed: Aug. 4, 2003

(65) Prior Publication Data

US 2004/0080713 A1    Apr. 29, 2004

(30) Foreign Application Priority Data

Aug. 14, 2002  (JP) .............................. 2002-236275

(51) Int. Cl.
*A61B 3/10* (2006.01)
*A61B 3/02* (2006.01)

(52) U.S. Cl. ...................... 351/221; 351/211; 351/205; 351/243

(58) Field of Classification Search ................ 351/205, 351/243, 246, 208, 221, 211, 212, 206, 247
See application file for complete search history.

(56) References Cited

U.S. PATENT DOCUMENTS

| | | | | |
|---|---|---|---|---|
| 5,141,304 A | * | 8/1992 | Ichihashi ..................... | 351/221 |
| 5,844,661 A | * | 12/1998 | Uchida et al. .............. | 351/211 |
| 5,929,970 A | * | 7/1999 | Mihashi ...................... | 351/205 |
| 6,361,168 B1 | * | 3/2002 | Fujieda ........................ | 351/208 |
| 6,802,609 B2 | * | 10/2004 | Mihashi et al. ............. | 351/221 |
| 6,905,209 B2 | * | 6/2005 | Mihashi et al. ............. | 351/221 |
| 2003/0189690 A1 | * | 10/2003 | Mihashi et al. ............. | 351/221 |

FOREIGN PATENT DOCUMENTS

| | | |
|---|---|---|
| JP | 2580215 B2 | 11/1996 |
| JP | 10-305013 | 11/1998 |
| JP | 2001-204690 | 7/2001 |
| JP | 2002-204784 A | 7/2002 |

* cited by examiner

*Primary Examiner*—Ricky Mack
*Assistant Examiner*—Brandi Thomas
(74) *Attorney, Agent, or Firm*—Foley & Lardner LLP

(57) ABSTRACT

A first movement unit for moving a condensing position so that a light flux from a light source is condensed on a place close to a retina of a subject eye, and a second movement unit for optically moving a conversion member for condensing a light flux reflected by the retina and a light receiving part for receiving light fluxes can be independently driven and can be further driven by an operation of an operator. First, an arithmetic part adjusts a projection side and a light receiving side based on first signals from the light receiving part. In a case where an independent mode is selected, the projection side and the light receiving side are adjusted automatically or manually. Further, the arithmetic part measures a characteristic of the eye in accordance with adjusted measurement conditions.

9 Claims, 21 Drawing Sheets

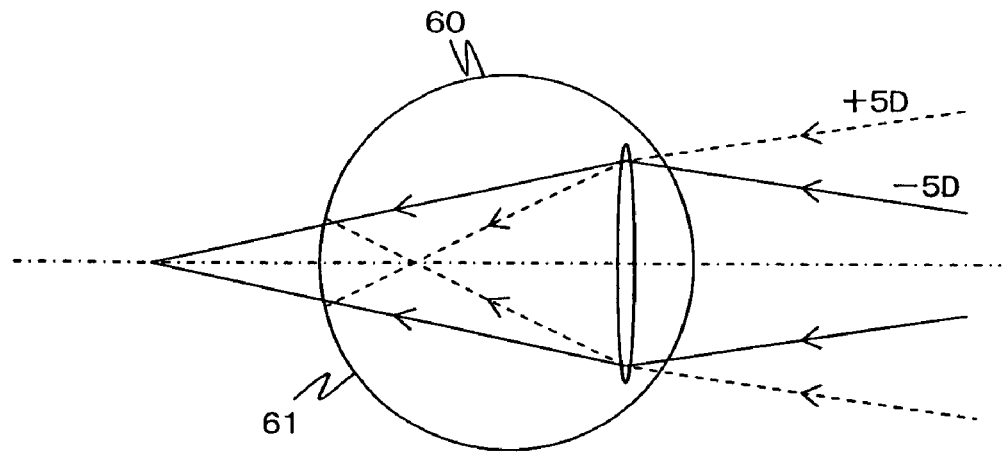
AT A TIME OF POSITIONAL DEVIATION OF
PROJECTION SIDE
(a)
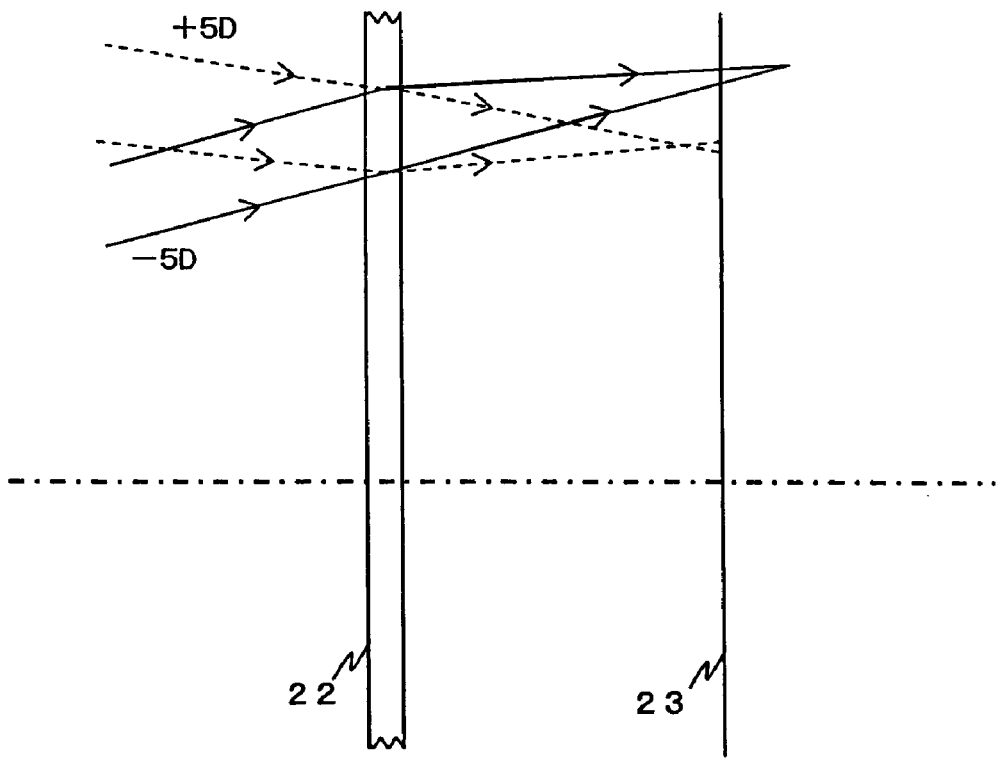
AT A TIME OF POSITIONAL DEVIATION OF
LIGHT RECEIVING SIDE
(b)
Fig.5

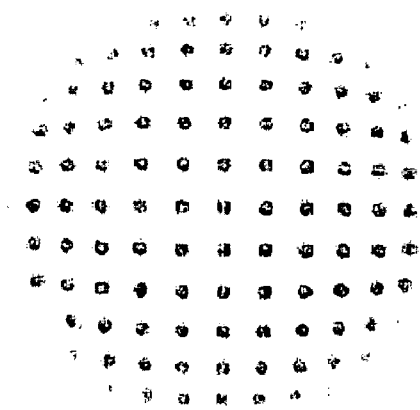
PROJECTION SIDE+ 5 D
(a)
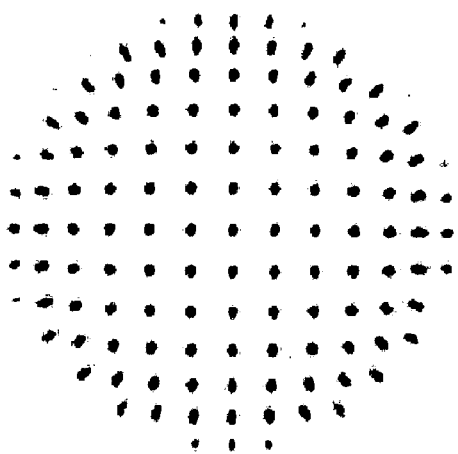
PROJECTION SIDE—5 D
(b)
Fig.6

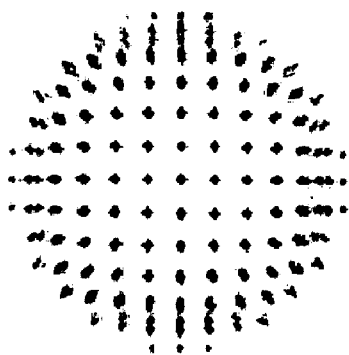
LIGHT RECEIVING SIDE+ 5 D
(a)
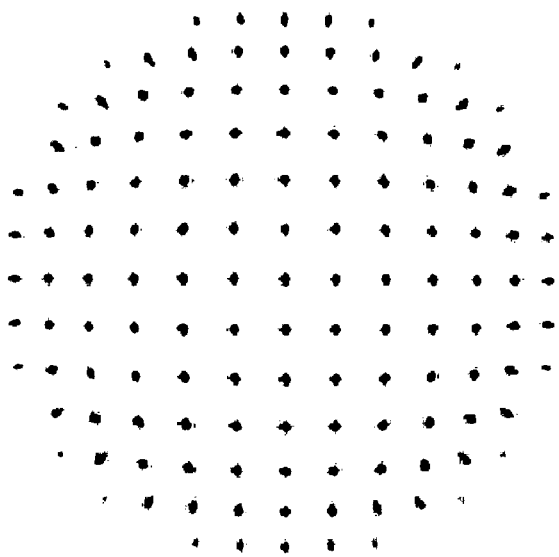
LIGHT RECEIVING SIDE− 5 D
(b)
Fig.7

$$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

Fig.13

$$\begin{array}{cc}
i & 2j-i \\
\end{array}
\begin{bmatrix}
0 & 0 & 1 \\
1 & -1 & y \\
1 & 1 & x \\
2 & -2 & 2yx \\
2 & 0 & 2x^2 + 2y^2 - 1 \\
2 & 2 & x^2 - y^2 \\
3 & -3 & 3yx^2 - y^3 \\
3 & -1 & 3yx^2 + 3y^3 - 2y \\
3 & 1 & 3x^3 + 3xy^2 - 2x \\
3 & 3 & x^3 - 3xy^2 \\
4 & -4 & 4yx^3 - 4y^3 x \\
4 & -2 & 8yx^3 + 8y^3 x - 6yx \\
4 & 0 & 6x^4 + 12x^2 y^2 + 6y^4 - 6x^2 - 6y^2 + 1 \\
4 & 2 & 4x^4 - 4y^4 - 3x^2 + 3y^2 \\
4 & 4 & x^4 - 6x^2 y^2 + y^4 \\
5 & -5 & 5yx^4 - 10y^3 x^2 + y^5 \\
5 & -3 & 15yx^4 + 10y^3 x^2 - 5y^5 - 12yx^2 + 4y^3 \\
5 & -1 & 10yx^4 + 20y^3 x^2 + 10y^5 - 12yx^2 - 12y^3 + 3y \\
5 & 1 & 10x^5 + 20x^3 y^2 + 10xy^4 - 12x^3 - 12xy^2 + 3x \\
5 & 3 & 5x^5 - 10x^3 y^2 - 15xy^4 - 4x^3 + 12xy^2 \\
5 & 5 & x^5 - 10x^3 y^2 + 5xy^4 \\
6 & -6 & 6yx^5 - 20y^3 x^3 + 6y^5 x \\
6 & -4 & 24yx^5 - 24y^5 x - 20yx^3 + 20y^3 x \\
6 & -2 & 30yx^5 + 60y^3 x^3 + 30y^5 x - 40yx^3 - 40y^3 x + 12yx \\
6 & 0 & 20x^6 + 60x^4 y^2 + 60x^2 y^4 + 20y^6 - 30x^4 - 60x^2 y^2 - 30y^4 + 12x^2 + 12y^2 - 1 \\
6 & 2 & 15x^6 + 15x^4 y^2 - 15x^2 y^4 - 15y^6 - 20x^4 + 20y^4 + 6x^2 - 6y^2 \\
6 & 4 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6 \\
\end{bmatrix}$$

Fig.14

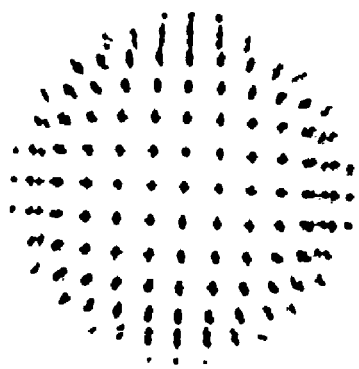
LIGHT RECEIVING SIDE 0 D
(a)
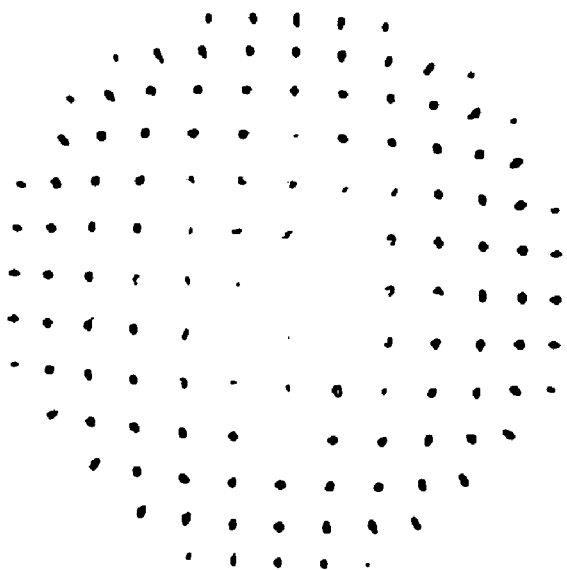
LIGHT RECEIVING SIDE − 5 D
(b)
Fig.21

OPHTHALMIC MEASURING APPARATUS

BACKGROUND OF THE INVENTION

The present invention relates to an ophthalmic measuring apparatus, and particularly to an ophthalmic measuring apparatus including a mechanism for independently adjusting an illuminating optical system and a light receiving optical system and having a refractive wavefront measuring function.

In recent years, an optical equipment used for medicine, especially in ophthalmology, becomes widespread as an optical characteristic measuring apparatus for testing an eye function, such as refractive power of an eye or adjustment thereof, and the inside of an eyeball. For example, there is an apparatus called a photo-refractometer for obtaining the refractive power of a subject eye and a corneal shape. For example, Japanese Patent Application No. 2000-351796 discloses an optical characteristic measuring apparatus for displaying measurement data (measurement result) obtained under plural conditions, image data and/or numerical data corresponding to the measurement result. In the conventional optical characteristic measuring apparatus, the subject eye is illuminated in an alignment adjustment, and an apparatus body is moved vertically and horizontally so that a spot image of a light flux reflected by the cornea becomes coincident with an optical axis. When the spot image becomes coincident with the optical axis, the optical characteristic measuring apparatus acquires a Hartmann image and an anterior eye image and signal processes them to measure the eye characteristics. In the measurement results of these various tests, it becomes important that for example, the subject eye of a patient as a test object is put in what measurement conditions.

However, since the conventional ophthalmic measuring apparatus having the refractive wavefront measuring function includes such a mechanism that the illuminating optical system and the light receiving optical system move together, in the case of an eye for which a normal measurement is difficult to perform, there has been a case where an obtained image becomes blurred and is not suitable for image analysis. For example, there is a case where ocular optical characteristics vary according to a place even in one eye, because of an operation, an external wound, an injury, a wound, or a disease. In such a case, in the conventional automatic measurement, there has been a case where a measurement result required by a doctor can not be obtained.

SUMMARY OF THE INVENTION

In view of the above circumstances, an object of the invention is to provide an ophthalmic measuring apparatus in which an operator operates to independently adjust an illuminating optical system and a light receiving optical system by an apparatus body, so that an obtained image can be adjusted to an image more suitable for analysis, and refractive wavefront measurements with high accuracy can be made.

According to first solving means of the invention, an ophthalmic measuring apparatus comprises a first illuminating optical system including a first light source for emitting a light flux of a first wavelength, for illuminating a retina of a subject eye, to be condensed on a place close to the retina, with the first illumination light flux from the first light source, a first light receiving optical system including a first conversion member for converting a reflected light flux reflected by the retina of the subject eye into at least 17 beams, and a first light receiving part for receiving the plural light fluxes converted by the first conversion member as first received light signals, for guiding the reflected light flux to the first light receiving part, first movement means for moving a condensing position of the first illuminating optical system, second movement means for optically moving the first light receiving part and the first conversion member, a mode changeover part for switching between an interlock mode in which movement operations of the first movement means and the second movement means are interlocked and an independent mode in which they can be independently controlled, and an arithmetic part for obtaining an optical characteristic of the subject eye by performing a Zernike analysis on the basis of tilt angles of the light fluxes obtained by the first light receiving part, wherein the first movement means and/or the second movement means can adjust the condensing position of the first illumination light flux and/or condensing positions of the light fluxes converted by the first conversion member according to received light positions and/or received light levels of the first received light signals at the first light receiving part.

According to second solving means of the invention, an ophthalmic measuring apparatus comprises a first illuminating optical system including a first light source for emitting a light flux of a first wavelength, for illuminating a retina of a subject eye, to be condensed on a place close to the retina, with the first illumination light flux from the first light source, a first light receiving optical system including a first conversion member for converting a reflected light flux reflected by the retina of the subject eye into at least 17 beams, and a first light receiving part for receiving the plural light fluxes converted by the first conversion member, for guiding the reflected light flux to the first light receiving part, first movement means for moving a condensing position of the first illuminating optical system, second movement means for optically moving the first light receiving part and the first conversion member, and an arithmetic part for obtaining an optical characteristic of the subject eye by combining tilt angle data of the light fluxes obtained by the first light receiving part under different conditions by the first movement means and the second movement means, and performing a Zernike analysis on the basis of the combined data.

BRIEF DESCRIPTION OF THE DRAWINGS

FIGS. 5A and 5B are explanatory views each showing an influence of positional deviation at the projection side and the light receiving side upon a Hartmann image.

FIGS. 6A and 6B are views each showing a Hartmann image at a time of occurrence of the positional deviation at the projection side.

FIGS. 7A and 7B are views each showing a Hartmann image at a time of occurrence of the positional deviation at the light receiving side.

FIG. 13 shows a Zernike polynomial expression (1).

FIG. 14 shows a Zernike polynomial expression (2).

FIGS. 21A and 21B are views each showing a Hartmann image of the ocular in which refractive power partially varies.

DETAILED DESCRIPTION OF THE INVENTION

Hereinafter, embodiments of the invention will be described in detail with reference to the drawings.

1. Structure of an Ophthalmic Measuring Apparatus

Figure 1:
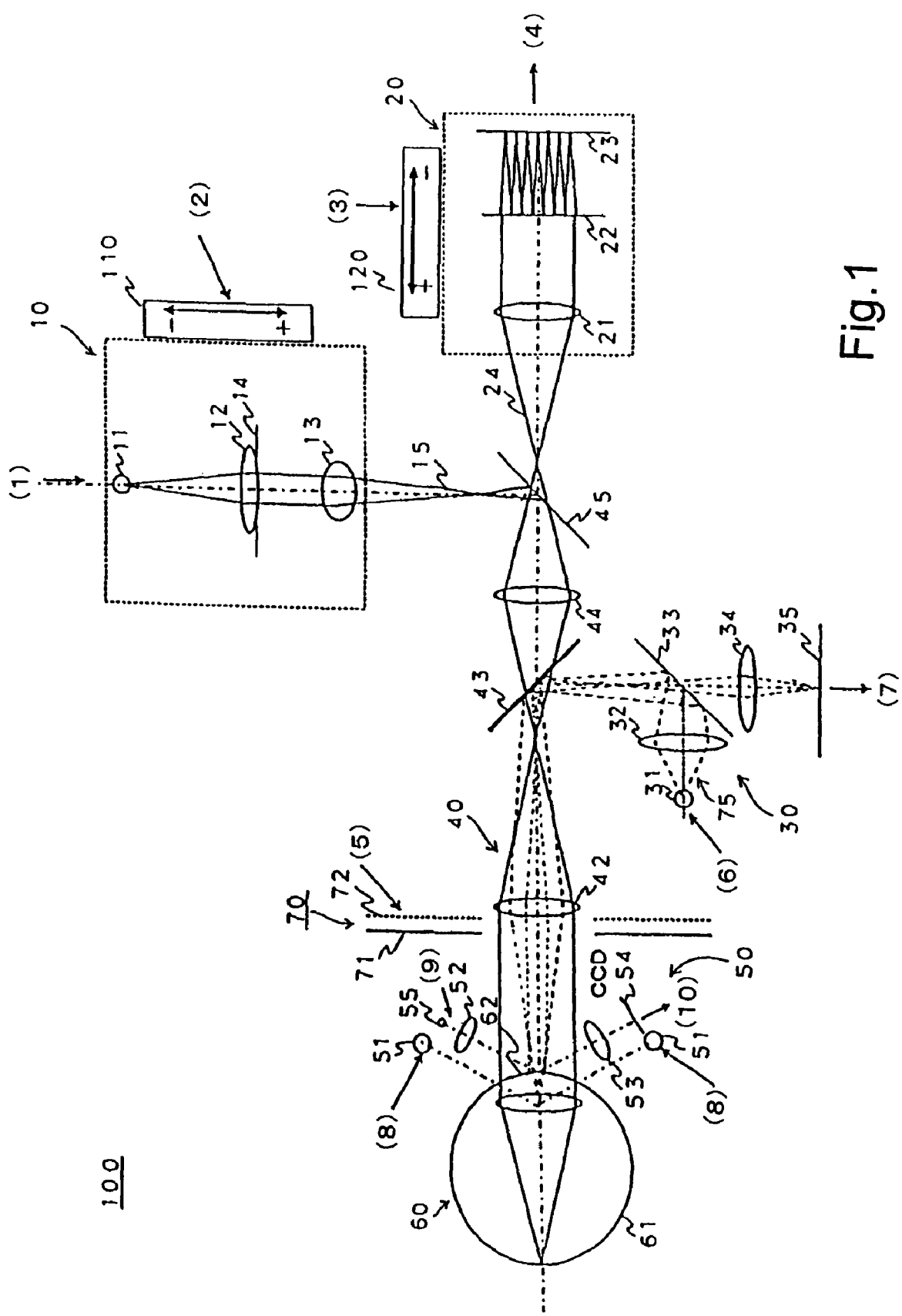
FIG. 1 is a view roughly showing an optical system 100 of an ophthalmic measuring apparatus of the invention.

FIG. 1 is a view roughly showing an optical system 100 of an ophthalmic measuring apparatus of the invention.

The optical system 100 of the ophthalmic measuring apparatus is an apparatus for measuring an optical characteristic of a subject eye 60 as an object, and includes a first illuminating optical system 10, a first light receiving optical system 20, a second light receiving optical system 30, a common optical system 40, an adjusting optical system 50, a second illuminating optical system 70, a third illuminating optical system 75, first movement means 110, and second movement means 120. Incidentally, with respect to the subject eye 60, a retina 61 and a cornea 62 are shown in the drawing.

The first illuminating optical system 10 includes, for example, a first light source 11 for emitting a light flux of a first wavelength, and a condensing lens 12, and is for illuminating a minute region on the retina (eyeground) 61 of the subject eye 60 with the light flux (first illumination light flux) from the first light source 11 so that its illumination condition can be suitably set. The first illuminating optical system 10 can move a condensing position by the first movement means 110.

The first wavelength of the first illumination light flux emitted from the first light source 11 is, as an example, a wavelength in an infrared range (for example, 780 nm). It is desirable that the first light source 11 has a large spatial coherence and a small temporal coherence. Here, the first light source 11 is, for example, a super luminescence diode (SLD), and a point light source having high luminescence can be obtained. Incidentally, the first light source 11 is not limited to the SLD, and for example, a laser having a large spatial coherence and a large temporal coherence can also be used by inserting a rotation diffused plate or the like to suitably lower the temporal coherence. Further, an LED having a small spatial coherence and a small temporal coherence can also be used, if light quantity is sufficient, by inserting, for example, a pinhole or the like at a position of a light source in an optical path.

The first light receiving optical system 20 includes, for example, a collimator lens 21, a Hartmann plate 22 as a conversion member for converting part of a light flux (first light flux) reflected and returned from the retina 61 of the subject eye 60 into at least 17 beams, and a first light receiving part 23 for receiving the plural beams converted by this Hartmann plate 22, and is for guiding the first light flux to the first light receiving part 23. The first light receiving optical system 20 can be moved by the second movement means 120 so that the beams converted by the Hartmann plate 22 are condensed on the first light receiving part 23. Besides, here, a CCD with little readout noise is adopted for the first light receiving part 23, and as the CCD, a suitable type of CCD, for example, a general low noise type of CCD, or a cooling CCD of 1000×1000 elements for measurement, can be applied. Signals (first received light signals) received by the first light receiving part 23 are used for obtaining, for example, an ocular higher order aberrations.

The first movement means 110 is for moving the first illuminating optical system, and is driven by, for example, a motor. The condensing position of the first illumination light flux from the first illuminating optical system can be adjusted by moving the first illuminating optical system by the first movement means 110.

The second movement means 120 is for moving the first light receiving optical system, and is driven by, for example, a motor. By moving the first light receiving optical system by the second movement means 120, an adjustment can be made such that the beams converted by the Hartmann plate 22 are condensed on the first light receiving part 23. Incidentally, a suitable apparatus and method can be used as the movement means of the first movement means 110 and the second movement means 120. Besides, in this embodiment, the first movement means 110 and the second movement means 120 can be driven together, and besides, they can be driven independently. Further, in addition of the automatic measurement by these movement means, the first movement means 110 and the second movement means 120 can be driven by the operation (manual operation) of an operator.

Figure 2:
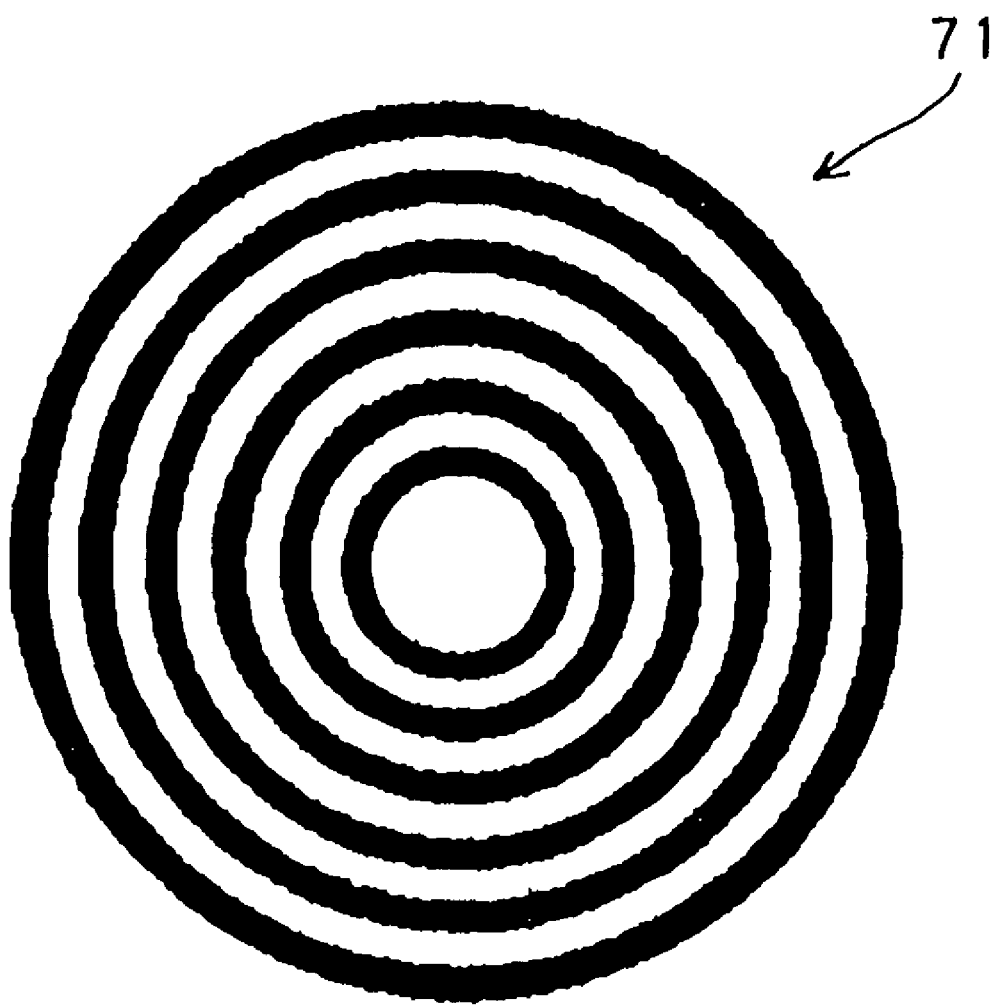
FIG. 2 is a structural view of a Placido's disk.

The second illuminating optical system 70 includes a second light source 72 for emitting a light flux of a second wavelength, and a Placido's disk 71. Incidentally, the second light source 72 can be omitted. FIG. 2 shows an example of a structural view of the Placido's disk 71. The Placido's disk (PLACIDO'S DISK) 71 is for projecting an index of a pattern composed of plural co-axial rings as shown in FIG. 2. Incidentally, the index of the pattern composed of the plural co-axial rings is an example of an index of a predetermined pattern, and a different suitable pattern can be used. Then, after an alignment adjustment described later is completed, the index of the pattern composed of the plural co-axial rings can be projected.

The third illuminating optical system 75 is for mainly performing, for example, the alignment adjustment described later, and includes a third light source 31 for emitting a light flux of a third wavelength, a condensing lens 32, and a beam splitter 33.

The second light receiving optical system 30 includes a condensing lens 34 and a second light receiving part 35. The second light receiving optical system 30 guides a light flux (second light flux), in which the pattern of the Placido's disk 71 illuminated from the second illuminating optical system 70 is reflected and returned from the anterior part or the cornea 62 of the subject eye 60, to the second light receiving part 35. Besides, the second light receiving optical system can guide a light flux (third light flux), which is emitted from the third light source 31 and is reflected and returned from the cornea 62 of the subject eye 60, to the second light receiving part 35. Incidentally, as the second wavelength and the third wavelength of the light fluxes emitted from the second light source 72 and the third light source 31, a wavelength different from, for example, the first wavelength (here, 780 nm) and long (for example, 940 nm) can be selected. Besides, the signal received by the second light receiving part 35 is used for, for example, the alignment adjustment or for obtaining corneal higher order aberrations.

The common optical system 40 is disposed on an optical axis of the light flux emitted from the first illuminating optical system 10, can be included in the first and the second illuminating optical systems 10 and 70, the first and the second light receiving optical systems 20 and 30, the third illuminating optical system 75, and the like, and includes, for example, an afocal lens 42, beam splitters 43 and 45, and a condensing lens 44. The beam splitter 43 is formed of such a mirror (for example, a dichroic mirror) that the wavelength of the third light source 31 is sent (reflected) to the subject eye 60, the second light flux and the third light flux reflected and returned from the cornea 62 of the subject eye 60 are reflected, and the wavelength of the first light source 11 is transmitted. The beam splitter 45 is formed of such a mirror (for example, a polarization beam splitter) that the wavelength of the first light source 11 is sent (reflected) to the subject eye 60, and the first light flux reflected and returned from the retina 61 of the subject eye 60 is transmitted. By the beam splitters 43 and 45, the first, the second and the third light fluxes do not mutually enter other optical systems to generate noise.

The adjusting optical system 50 is for mainly performing, for example, an operation distance adjustment, and includes a fourth light source 51, a fifth light source 55, condensing lenses 52 and 53, and a third light receiving part 54. The operation distance adjustment is performed in such a way that for example, a parallel light flux in the vicinity of an optical axis emitted from the fifth light source 55 is irradiated to the subject eye 60, and the light reflected from this subject eye 60 is received by the third light receiving part 54 through the condensing lenses 52 and 53. Besides, in the case where the subject eye 60 is in a suitable operation distance, a spot image from the fifth light source 55 is formed on the optical axis of the third light receiving part 54. On the other hand, in the case where the subject eye 60 is not within the suitable operation distance, a spot image from the fifth light source 55 is formed above or below the optical axis of the third light receiving part 54. Incidentally, since the third light receiving part 54 has only to detect the change of a light flux position on the plane including the fifth light source 55, the optical axis, and the third light receiving part 54, for example, a one-dimensional CCD, a position selecting device (PSD) or the like disposed on this plane can be applied.

Next, the alignment adjustment will be described. The alignment adjustment is mainly carried out by the second light receiving optical system 30 and the third illuminating optical system 75.

First, the light flux from the third light source 31 illuminates the subject eye 60 as the object with the parallel light flux through the condensing lens 32, the beam splitters 33 and 43, and the afocal lens 42. The reflected light flux reflected by the cornea 62 of the subject eye 60 is emitted as a divergent light flux such as is emitted from a point of the half of the radius of curvature of the cornea 62. The divergence light flux is received as the spot image by the second light receiving part 35 through the afocal lens 42, the beam splitters 43 and 33, and the condensing lens 34.

Here, in the case where the spot image on the second light receiving part 35 is out of the optical axis, the optical characteristic measuring apparatus body is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the subject eye 60 is illuminated with the fourth light source 51, and the image of the subject eye 60 obtained by this illumination is formed on the second light receiving part 35, and accordingly, the center of the pupil may be made to coincide with the optical axis by using this image.

Next, a positional relation between the first illuminating optical system 10 and the first light receiving optical system 20 will be roughly described.

The beam splitter 45 is inserted in the first light receiving optical system 20, and by this beam splitter 45, the light from the first illuminating optical system 10 is sent to the subject eye 60, and the reflected light from the subject eye 60 is transmitted. The first light receiving part 23 included in the first light receiving optical system 20 receives the light transmitted through the Hartmann plate 22 as the conversion member and generates the received light signal.

The first light source 11 and the retina 61 of the subject eye 60 form a conjugated relation. The retina 61 of the subject eye 60 and the first light receiving part 23 are conjugate. Besides, the Hartmann plate 22 and the pupil of the subject eye 60 form a conjugated relation. Further, in the first light receiving optical system 20, the pupil and the Hartmann plate 22 form substantially the conjugated relation. That is, the front focal point of the afocal lens 42 substantially coincides with the pupil.

The lens 12 converts a diffused light of the light source 11 into a parallel light. A diaphragm 14 is positioned at an optically conjugated position with respect to the pupil of the eye and the Hartmann plate 21. The diaphragm 14 has a diameter smaller than an effective range of the Hartmann plate 21, and the so-called single path aberration measurement (method in which the aberration of an eye influences on only the light receiving side) is established. In order to satisfy the above, the lens 13 is disposed such that the conjugated point of the retina of the real light beam coincides with the front focal position, and in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, at the single path measurement, the diameters of the light beams are different from each other, and the beam diameter of the light beam 15 is set to be rather small as compared with the light beam 24. Specifically, the beam diameter of the light beam 15 is about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis are applied to the Hartmann plate 22. Besides, in general, with respect to a measurement object part (subject eye 60), in order to measure a spherical component of the subject eye 60, a third order astigmatism, and other higher order aberrations, it is necessary to perform the measurement with at least 17 beams through the subject eye 60.

The micro-Fresnel lens is an optical element, and includes, for example, a ring of a height pitch for each wavelength, and a blade optimized for emission parallel to a condensing point. The micro-Fresnel lens here is subjected to, for example, optical path length difference of 8 levels applied by a semiconductor fine working technique, and achieves a high condensing efficiency (for example, 98%).

Besides, the reflected light from the retina 61 of the subject eye 60 passes through the afocal lens 42, the collimate lens 21, and is condensed on the first light receiving part 23 through the Hartmann plate 22. Accordingly, the Hartmann plate 22 includes a wavefront conversion member for converting the reflected light flux into at least 17 beams.

Figure 3:
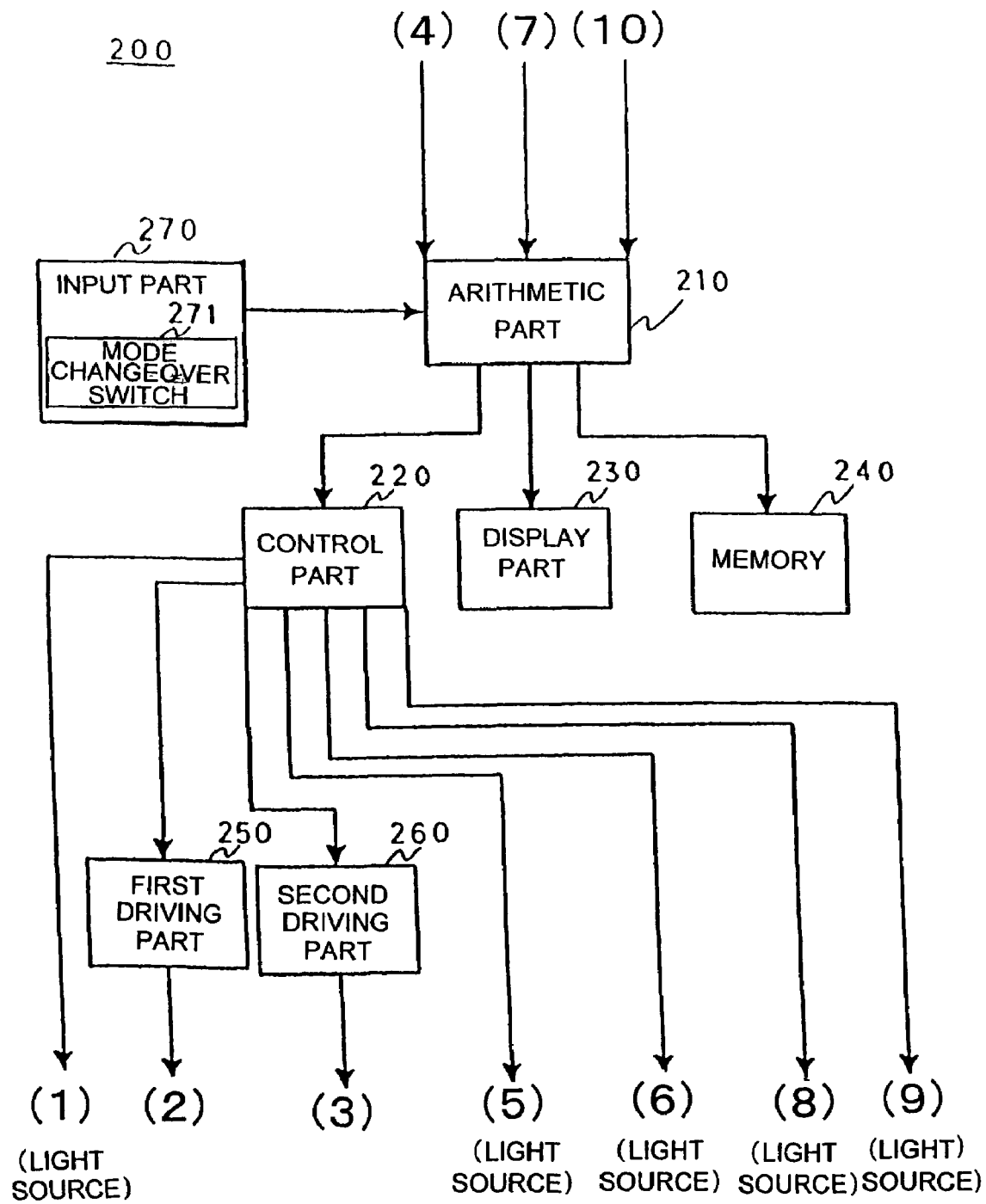
FIG. 3 is a block diagram roughly showing an electrical system 200 of the ophthalmic measuring apparatus of the invention.

FIG. 3 is a block diagram roughly showing an electrical system 200 of the ophthalmic measuring apparatus of the invention. The electrical system 200 of the ophthalmic measuring apparatus includes, for example, an arithmetic part 210, a control part 220, a display part 230, a memory 240, a first driving part 250, a second driving part 260, and an input part 270.

The arithmetic part 210 receives a received light signal (4) obtained from the first light receiving part 23, a received light signal (7) obtained from the second light receiving part 35, and a received light signal (10) obtained from the third light receiving part 54, and calculates an ocular aberrations, Zernike coefficients and the like. Further, the arithmetic part 210 receives input signals of desired setting, instructions, data and the like from the input part 270. Besides, the arithmetic part 210 calculates corneal aberrations, aberration coefficients, white light MTF (Modulation Transfer Function) as an index expressing the transmission characteristics of a spatial frequency, a Strehl ratio obtained by dividing the center intensity of a point image intensity distribution PSF (Point Spread Function) by the center intensity of the PSF obtained in the case of astigmatic optical system, a Landolt's ring pattern having a size corresponding to suitable visual acuity for testing the visual acuity of a patient, and the like. Besides, signals corresponding to such calculation results are outputted to the control part 220 for performing the whole control of an electric driving system, the display part 230, and the memory 240, respectively.

The control part 220 controls lighting and lights-out of the first light source 11 on the basis of the control signal from the arithmetic part 210, or controls the first driving part 250 and the second driving part 260. For example, on the basis of the signals corresponding to the calculation results in the arithmetic part 210, the control part outputs a signal (1) to the first light source 11, outputs a signal (5) to the Placido's disk 71, outputs a signal (6) to the third light source 31, outputs a signal (8) to the fourth light source 51, outputs a signal (9) to the fifth light source 55, and outputs signals to the first driving part 250 and the second driving part 260.

The first driving part 250 is for moving the whole first illuminating optical system 10 in the optical axis direction to move the condensing position on the basis of, for example, the received light signal (4) from the first light receiving part 23 inputted to the arithmetic part 210 or the movement signal inputted from the input part 270, and outputs a signal (2) to the first movement means 110 to drive this movement means. By this, the first driving part 250 can perform the movement and adjustment of the first illuminating optical system 10.

The second driving part 260 is for moving the whole first light receiving optical system 20 in the optical axis direction on the basis of, for example, the received light signal (4) from the first light receiving part 23 inputted to the arithmetic part 210 or the input signal inputted from the input part 270, and outputs a signal (3) to the second movement means 120 to drive this movement means. By this, the second driving part 260 can perform the movement and adjustment of the first light receiving optical system 20.

The input part 270 includes a switch, a button, a keyboard, a pointing device and the like for inputting various input signals of desired setting, instructions, data and the like. For example, the input part 270 includes a mode changeover switch 271, an operation changeover switch, a measurement start button, and a movement switch for moving the first illuminating optical system 10 or the first light receiving optical system 20 in a + direction and a − direction. The mode changeover switch 271 is a switch for switching between an interlock mode in which the first illuminating optical system 10 and the first light receiving optical system 20 are moved together, and an independent mode in which they are independently moved. The operation changeover switch is a switch for switching between a measurement by automatic adjustment and a measurement by manual adjustment. The movement switch includes, for example, a projection side movement switch for moving the first illuminating optical system 10, and a light receiving side movement switch for moving the first light receiving optical system 20. At the time of selection of the manual adjustment, by operating the movement switch, the operator drives the first movement means 110 and the second movement means 120 through the first driving part 250 and the second driving part 260 by the control of the arithmetic part 210 and the control part 220, and can independently move the first illuminating optical system 10 and the first light receiving optical system 20 in the + direction and the − direction. Incidentally, a diopter value may be changed by an amount of set step (for example, 0.25 diopter) for one input of the movement switch, and the first illuminating optical system 10 and the first light receiving optical system 20 are moved in a specified direction. Besides, the operator may specify the diopter values of the first illuminating optical system side and the first light receiving optical system side by a keyboard. In this case, by the control of the arithmetic part 210 and the control part 220, the first movement means 110 and the second movement means 120 are driven through the first driving part 250 and the second driving part 260, and the first illuminating optical system 10 and the first light receiving optical system 20 are moved to positions corresponding to the specified diopter values. Incidentally, as a specifying method and input means of the diopter values, a suitable one can be used.

Next, a Zernike analysis will be described. A method of calculating Zernike coefficients $C_n^m$ from a generally known Zernike polynomial expression will be described. The Zernike coefficients $C_n^m$ are an important parameter for grasping the optical characteristic of the subject eye 60 on the basis of tilt angles of light fluxes obtained by the first light receiving part 23 through the Hartmann plate 22.

A wavefront aberrations W(X, Y) of the subject eye 60 is expressed by the following expression using the Zernike coefficients $C_i^{2j-i}$ and the Zernike polynomial expression $Z_i^{2j-i}$.

$$W(X, Y) = \sum_{i=0}^{n} \sum_{j=0}^{i} c_i^{2j-i} Z_i^{2j-i}(X, Y) \quad \text{[Numerical Expression 1]}$$

Where, (X, Y) denotes vertical and horizontal coordinates of the Hartmann plate 22. Besides, in the above expression, n denotes an analysis order.

Besides, with respect to the wavefront aberrations W(X, Y), when the vertical and horizontal coordinates of the first light receiving part 23 is (x, y), the distance between the Hartmann plate 22 and the first light receiving part 23 is f, and the movement distance of a point image received by the first light receiving part 23 is ($\Delta$x, $\Delta$y), the relation of the following expression is established.

$$\frac{\partial W(X, Y)}{\partial X} = \frac{\Delta x}{f} \quad \text{[Numerical Expression 2]}$$
$$\frac{\partial W(X, Y)}{\partial Y} = \frac{\Delta y}{f}$$

Here, the Zernike polynomial expression $Z_n^m$ is expressed by the following numerical expression 3, and is specifically shown in FIGS. 13 and 14. Where, n and m correspond to i and 2j-i in FIGS. 13 and 14.

$$Z_n^m = R_n^m(r) \left\{ \begin{array}{c} \sin \\ \cos \end{array} \right\} \{m\theta\} \quad \text{[Numerical Expression 3]}$$
$$m > 0 \; \sin$$
$$m \leq 0 \; \cos$$
$$R_n^m(r) = \sum_{S=0}^{(n-m)/2} (-1)^S \frac{(n-S)!}{S!\left\{\frac{1}{2}(n-m)-S\right\}! \left\{\frac{1}{2}(n+m)-S\right\}!} r^m$$

Incidentally, specific values of the Zernike coefficients $C_n^m$ can be obtained by minimizing a square error expressed by following numerical expression 4.

$$S(x) = \sum_{i=1}^{\text{data number}} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad \text{[Numerical Expression 4]}$$

Where, W(X, Y): wavefront aberrations, (X, Y): Hartmann plate coordinates, ($\Delta$x, $\Delta$y): movement distance of the point image received by the first light receiving part 23, and f: distance between the Hartmann plate 22 and the first light receiving part 23.

The arithmetic part 210 calculates the Zernike coefficients $C_n^m$, and uses these to obtain the optical characteristic of the eye, such as a spherical aberration, a coma aberration, and an astigmatic aberration.

2. Influence of Positional Deviation of the Illuminating Optical System and the Light Receiving Optical System Next, a description will be given of an influence on a Hartmann image in a case where diopter values of the first illuminating optical system 10 (projection side) and the first light receiving optical system 20 (light receiving side) are deviated.

Figure 4:
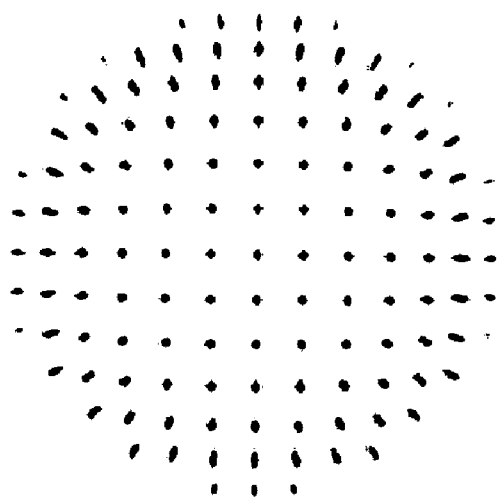
FIG. 4 is a view showing a Hartmann image in a case where there is no positional deviation in a projection side and a light receiving side.

FIG. 4 is a view of a Hartmann image in the case where there is no positional deviation at the projection side and the light receiving side. The drawing shows the Hartmann image in the case where a light flux emitted from the first illuminating optical system 10 is reflected by the retina 61 of the subject eye 60 and is condensed on the first light receiving part 23, that is, in the case where there is no positional deviation at the projection side and the reception side.

FIGS. 5A and 5B are explanatory views each showing an influence on the Hartmann image due to positional deviation of the projection side or the light receiving side. Hereinafter, with reference to FIGS. 5A and 5B, the Hartmann images shown in FIGS. 6A and 6B and FIGS. 7A and 7B will be described.

FIGS. 6A and 6B are views each showing the Hartmann image at the time of the occurrence of positional deviation of the projection side. FIG. 6A shows the Hartmann image in the case where only the projection side is deviated from the state of FIG. 4 by +5 diopters (+5D). When the projection side is deviated in the + direction, as indicated by a broken line of FIG. 5A, since the light flux emitted from the first illuminating optical system 10 is incident from the outside of the center axis toward the inside direction, it is condensed in front of the retina 61 of the subject eye 60. Since the light flux not condensed is reflected by the retina 61, when the reflected light flux is received by the first light receiving part 23, the point image of a received light signal becomes blurred, and the received light level (light quantity) of the received light signal becomes low.

On the other hand, FIG. 6B shows the Hartmann image in the case where only the projection side is deviated from the state of FIG. 4 by −5 diopters (−5D). When the projection side is deviated in the − direction, as indicated by a solid line of FIG. 5A, since the light flux emitted from the first illuminating optical system 10 is incident from the inside of the center axis toward the outside direction, the light flux is condensed at the rear of the retina 61 of the subject eye 60. Similarly to the case where the projection side is deviated in the + direction, since the light flux not condensed is reflected by the retina 61, when the reflected light flux is received by the first light receiving part 23, the point image of a received light signal becomes blurred, and the received light level of the received light signal becomes low.

As stated above, the projection side relates to the received light level of the point image of the received light signal received by the first light receiving part 23. That is, when the projection side is moved, the point image can be blurred or sharpened. In order to enhance the received light level, the projection side is moved in one of the + direction and the − direction in which the received light level becomes large. In the automatic adjustment, the arithmetic part 210 moves the first illuminating optical system 10 on the basis of the received light signal of the first light receiving part 23 so that the received light level of the point image becomes large, and the diopter value of the projection side is adjusted.

FIGS. 7A and 7B are views each showing a Hartmann image at the time of the occurrence of positional deviation at the light receiving side. FIG. 7A shows the Hartmann image in the case where only the light receiving side is deviated from the state of FIG. 4 by +5D. When the light receiving side is deviated in the + direction, as indicated by a broken line of FIG. 5B, since a light flux reflected by the retina 61 is incident on the Hartmann plate 22 from the outside of the center axis toward the inside direction, not in the vertical direction, it is condensed on a place closer to the center axis, and reaches the first light receiving part. The point images received by the first light receiving part 23 are collected in a place closer to the center axis on the whole, and become, as shown in FIG. 7A, images in which point image intervals are small.

On the other hand, FIG. 7B shows the Hartmann image in the case where only the light receiving side is deviated from the state of FIG. 4 by −5D. When the light receiving side is deviated in the − direction, as indicated by a solid line of FIG. 5B, the light flux reflected by the retina 61 is incident on the Hartmann plate 22 from the inside of the center axis toward the outside direction, not in the vertical direction, and it is condensed apart from the center axis. The point images received by the first light receiving part 23 go away from the center axis on the whole, and become images as shown in FIG. 7B in which point image intervals are large.

As stated above, the light receiving side relates to the point image intervals of the point images received by the first light receiving part 23. That is, the light receiving side is moved in the − direction in the case where the point image intervals are small, and the light receiving side is moved in the + side in the case where the point image intervals are large, so that the correction to a suitable diopter value can be made. In the automatic adjustment, the arithmetic part 210 moves the first light receiving optical system side on the basis of the received light signal of the first light receiving part 23 so that the point image interval becomes a predetermined interval, and the diopter value at the light receiving side is adjusted.

Figure 8:
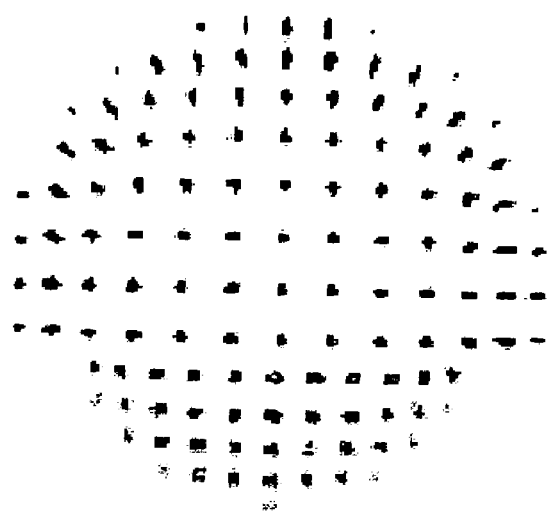
FIG. 8 is a view showing a Hartmann image of an ocular having irregular optical characteristics.

FIG. 8 is a view showing the Hartmann image of an eye having irregular optical characteristics by the influence of an operation, a disease, a wound, an injury or the like. The Hartmann image shown in FIG. 8 is an example of an ocular in which the optical characteristic of the upper half is different from that of the lower half. In this example, since an adjustment of a diopter value is performed for only the upper half, the point image interval of the lower half is narrow, that is, the measurement is made in the state where the light receiving side is deviated. In such an eye, since the point image interval of the lower half is narrow, there is a case where the measurement is difficult in the conventional ophthalmic measuring apparatus, and it becomes necessary to make a fine adjustment. In this embodiment, even for such an eye, the correction of the Hartmann image is enabled by finely adjusting the diopter value by a manual operation, and high accuracy measurement becomes possible. For example, like the Hartmann image of FIG. 8, in the case where although suitable measurement of the optical characteristic can be made in the upper half, the point image interval of the lower half is narrow and suitable measurement can not be made, the point image interval can be made wide by moving the light receiving side in one direction. By this, although the point image interval of the upper half becomes wide, the Hartmann image suitable for analysis can be detected on the whole, and the optical characteristic can be obtained by the arithmetic part 210. Besides, in the case where the lower half is blurred so that the suitable measurement can not be made, the projection side is shifted in the + direction or the − direction to sharpen the point image, and it is possible to achieve such a state that suitable measurement can be made for both the upper half and the lower half.

3. Operation Mode

This embodiment includes the interlock mode in which the first illuminating optical system 10 and the first light receiving optical system 20 are moved together, and the independent mode in which the first illuminating optical system 10 and the first light receiving optical system 20 are independently moved, and these can be switched by the mode changeover switch 271 of the input part 270. Further, in the independent mode, it is possible to select a case where the first illuminating optical system 10 and the first light receiving optical system 20 are separately automatically adjusted, and a case where a manual adjustment is made by an operator.

In the interlock mode, the first illuminating optical system 10 and the first light receiving optical system 20 are moved together so that the signal level of the reflected light at the first light receiving part 23 becomes maximum under the assumption that the light flux from the first light source 11 is reflected at a point on which the light is condensed. Specifically, the first illuminating optical system 10 and the first light receiving optical system 20 are moved in the direction where the signal level at the first light receiving part 23 becomes large, and are stopped at the position where the signal level becomes maximum. By this, the light flux from the first light source 11 is condensed on the subject eye 60. Incidentally, the first illuminating optical system 10 and the first light receiving optical system 20 may be moved by use of a suitable index other than the signal level.

In the automatic adjustment of the independent mode, the first illuminating optical system 10 and the first light receiving optical system 20 are independently moved. On the basis of the first received light signal at the first light receiving part 23, the arithmetic part 210 obtains intervals of point images, and the second movement means 120 moves the first light receiving part 23 toward the minus side in the case where a region narrower than a predetermined interval range exists in the point image intervals, and toward the plus side in the case where a region wider than the predetermined interval range exists therein. Besides, the arithmetic part 210 causes the first movement means 110 to move the first illuminating optical system 10 so that the signal level of the first received light signal at the first light receiving part 23 falls within a predetermined level range or becomes maximum. Incidentally, the predetermined interval range and the predetermined level range may be previously set and stored in the memory 240 or the like. Besides, these ranges may be suitably changed by the input part 270.

In the manual adjustment of the independent mode, the first illuminating optical system 10 and the first light receiving optical system 20 can be moved to arbitrary diopter positions by a projection side and a light receiving side movement switches. At the time of independent mode selection, the mode becomes the manual wavefront measuring mode by the operation changeover switch. In the manual wavefront measuring mode, for example, refractive measurement and kerato-measurement by the interlock mode is performed, and after the measurement is ended, it is stopped and is put in the manual adjustment state.

Figure 9:
FIG. 9 is a display view in a manual adjustment state.

FIG. 9 is a display view in the manual adjustment state. At this time, the arithmetic part 210 displays diopter values (S1: projection side, S2: light receiving side) for manual wavefront measurement on the display part 230. As the initial values of the diopter values to be displayed, the diopter values under which the refractive measurement and kerato-measurement by the interlock mode was performed may be used. Besides, in addition to the diopter values, an astigmatism degree C., an astigmatism axis A, and other suitable parameters may be further displayed. Moreover, the arithmetic part 210 captures the first received light signal concerning the Hartmann image from the first light receiving part 23, and displays the Hartmann image on the display part 230. The arithmetic part 210 captures the first received light signal from the first light receiving part 23 every predetermined period or each time the diopter value is changed by a manual operation, and may update the display of the Hartmann image.

At the time of the manual adjustment state, the operator can move the projection side and the light receiving side to arbitrary diopter positions by the projection side and the light receiving side movement switches or the input part 270 such as a keyboard. The projection side is moved in the + direction by the projection side + movement switch, and is moved in the − direction by the projection side − movement switch. By the movement of the projection side, the point image can be blurred or sharpened. Similarly, the light receiving side is moved in the + direction by the light receiving side + movement switch, and is moved in the − direction by the light receiving side − movement switch. When the light receiving side is moved, the point image interval can be widened or narrowed. When the switch input is performed, the arithmetic part 210 changes the diopter value in the + direction or the − direction by a step amount (for example, 0.25 diopter) previously set for one switch input. The arithmetic part 210 changes the diopter values S1 and S2 displayed on the display part 230. Besides, the arithmetic part 210 moves the first illuminating optical system 10 and the first light receiving optical system 20 through the first driving part 250 and the second driving part 260 in accordance with the changed diopter values. When the setting of the diopter values is completed, a measurement start switch is pressed so that the wavefront measurement is started.

Besides, the operator may specify the diopter values by the keyboard or the like of the input part 270. When the diopter values are inputted from the input part 270, the arithmetic part 210 changes the diopter values S1 and S2 displayed on the display part 230, and performs such a control that the first illuminating optical system 10 and the first light receiving optical system 20 are automatically moved to positions corresponding to the inputted diopter values by the first movement means 110 and the second movement means 120 through the control part 220, the first driving part 250 and the second driving part 260.

4. Flowchart

Figure 10:
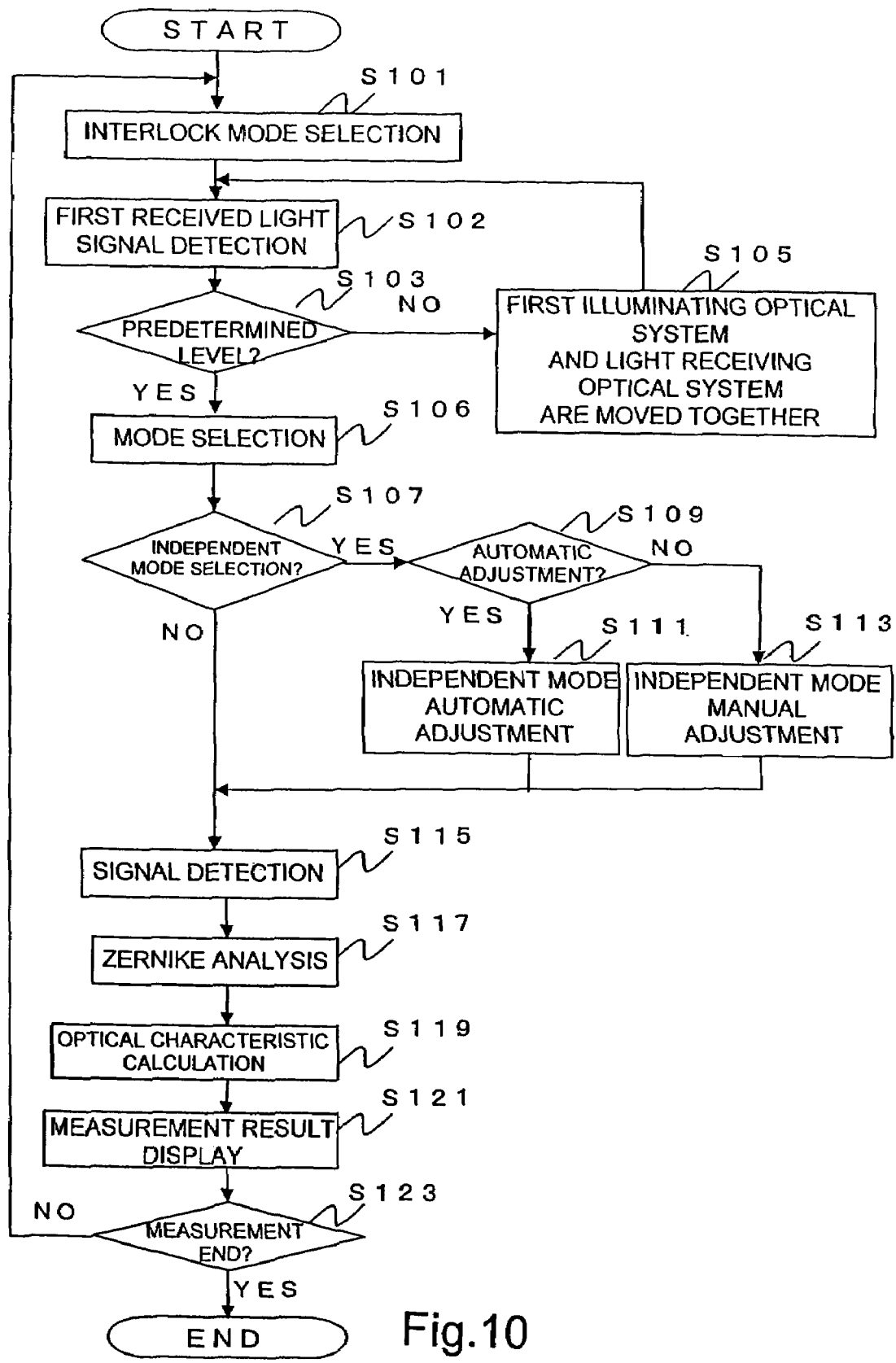
FIG. 10 is a flowchart showing an operation of the ophthalmic measuring apparatus having a manual wavefront measuring function.
Figure 11:
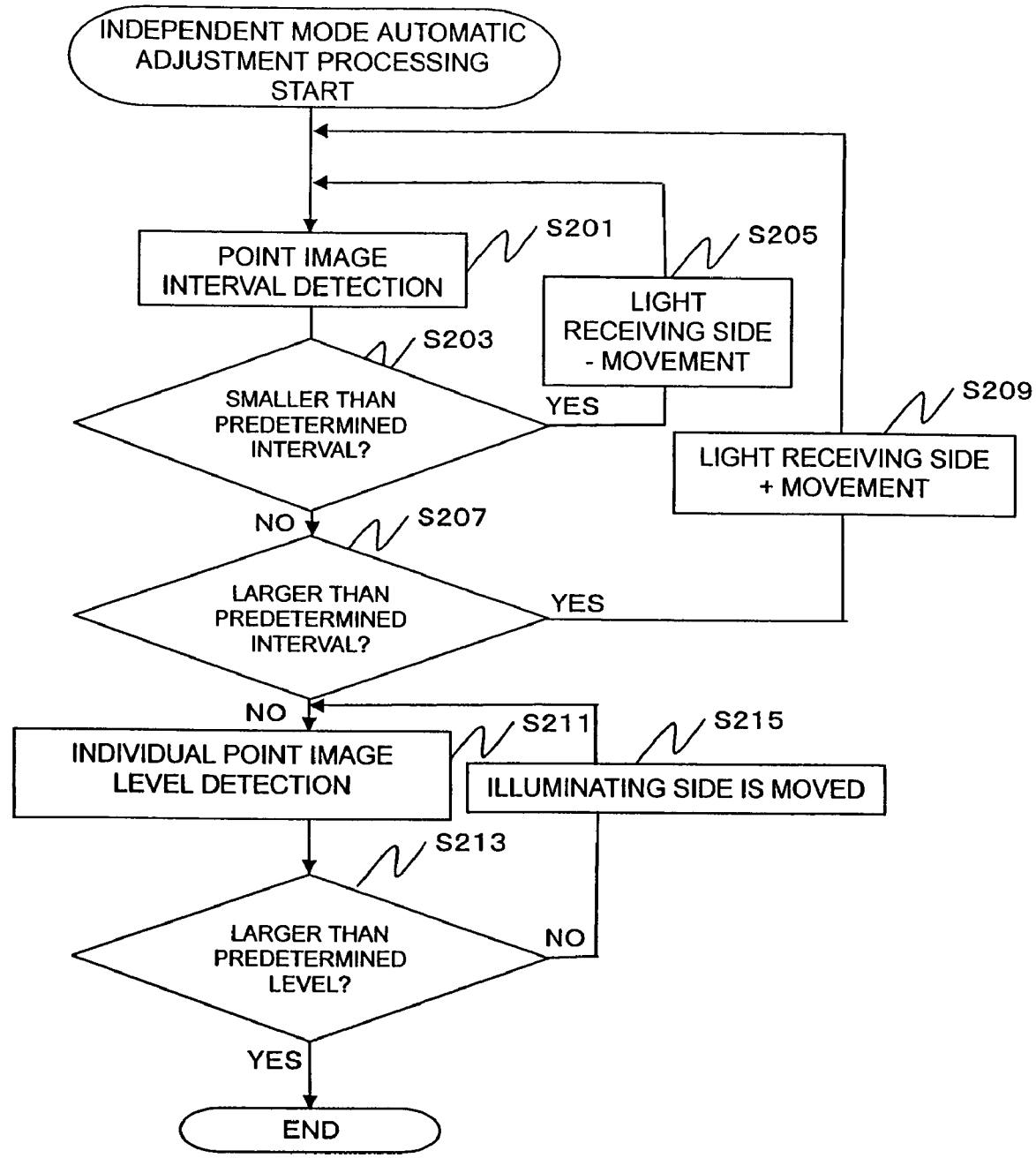
FIG. 11 is a flowchart of an independent mode automatic adjustment processing.
Figure 12:
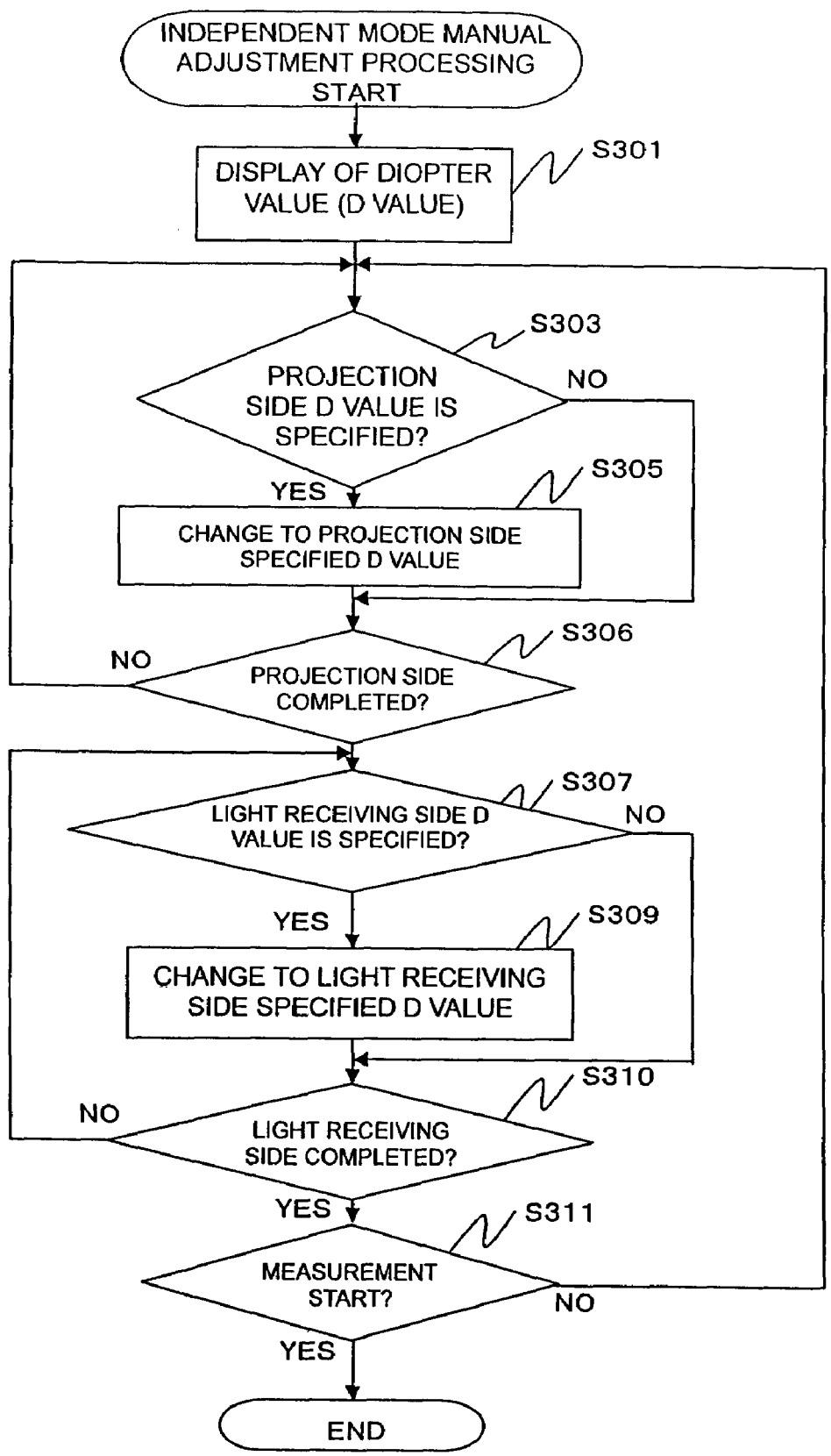
FIG. 12 is a flowchart of an independent mode manual adjustment processing.

FIGS. 10 to 12 are flowcharts showing the operation of the ophthalmic measuring apparatus including the optical independent adjustment mechanism and having the wavefront measuring function.

First, in the case of the interlock mode as a preset, the arithmetic part 210 selects the interlock mode in which the first illuminating optical system 10 and the first light receiving part 23 are moved together, and performs the alignment adjustment (S101). Besides, the arithmetic part 210 displays a menu for selection of the interlock mode and the independent mode on the display part 230, and the mode selection signal may be inputted from the mode changeover switch 271 of the input part 270. In that case, after the alignment adjustment is performed, the arithmetic part 210 proceeds to a processing of step S103 at the time of interlock mode selection, or proceeds to a processing of step S109 at the time of independent mode selection.

The arithmetic part 210 captures the first received light signal concerning the Hartmann image by using the first light receiving part 23 of low noise CCDs or the like (S102). The arithmetic part 210 obtains an average of the received light signal levels concerning the inputted first received light signals. Further, the arithmetic part 210 reads a predetermined signal level from the memory 240, and judges whether the average of the received light signal levels is the predetermined signal level (S103). Incidentally, the predetermined signal level is previously set and is stored in the memory 240. The arithmetic part 210 proceeds to a processing of step S106 in the case where the average received light signal level is the predetermined signal level. Incidentally, at the step S103, in addition to the average of the received light signal levels, a suitable value such as a minimum value, a maximum value, or a sum may be used. Besides, the arithmetic part 210 may input diopter values measured by a refractometer installed in the apparatus or diopter values measured by a different refractometer after the step S101, and moves the first illuminating optical system 10 and the first light receiving part 23 to positions corresponding to the inputted diopter values by the first movement means 110 and the second movement means 120.

In the case where the average received light signal level is not the predetermined signal level, the arithmetic part 210 outputs movement signals to move the first illuminating optical system 10 and the first light receiving part 23 to the first driving part 250 and the second driving part 260 automatically or by instructions from the input part 270, and returns to the processing of the step S102 (S105). The first driving part 250 and the second driving part 260 receive the movement signals from the arithmetic part 210, and in accordance with the inputted signals, they move the first illuminating optical system 10 and the first light receiving part 23 together by the first movement means 110 and the second movement means 120.

Next, in the case where the average received light signal level is the predetermined signal level, the arithmetic part 210 displays a menu for instructions of input as to whether the independent mode is selected or the automatic mode is selected on the display part 230, and the mode selection signal is inputted from the mode changeover switch 271 of the input part 270 (S106). This selection can be automatically judged by the number of point images (points) in which the received light level reaches the predetermined signal level. The arithmetic part 210 judges whether the inputted mode selection signal indicates the selection of the independent mode (S107). Incidentally, as the input of the mode selection signal, a suitable method can be used in addition to the input by the switch. In the case where the independent mode is selected, the arithmetic part 210 proceeds to a processing of step S109, and in the case where the independent mode is not selected, it proceeds to a processing of step S115. Besides, it may proceed to a predetermined mode after time is up.

Further, the arithmetic part 210 displays the menu for instructions of the input as to whether the adjustment of the projection side and the light receiving side is the automatic adjustment or the manual adjustment on the display part 230, and the operation selection signal is inputted from the operation changeover switch of the input part 270. The arithmetic part 210 judges whether the inputted operation selection signal indicates the automatic adjustment or the manual adjustment (S109). Incidentally, as the input of the operation selection signal, a suitable method can be used in addition to the input by the switch.

In the case where the judgment of the automatic adjustment is made (S109), the arithmetic part 210 performs the independent mode automatic adjustment processing (S111). In the independent mode automatic adjustment processing, the first light receiving part 23 is moved in accordance with the point image intervals of the first received light signals captured from the first light receiving part 23, and the first illuminating optical system 10 is moved in accordance with the point image levels. By independently moving the first light receiving part 23 and the first illuminating optical system 10, it becomes possible to perform the measurement suitable for the ocular.

FIG. 11 is a flowchart of the independent mode automatic processing. Hereinafter, the independent mode automatic adjustment processing of the step S111 will be described.

First, the arithmetic part 210 reads the first received light signals from the first light receiving part 23, and on the basis of the captured first received light signals, it detects the intervals of the respective point images, and obtains the average of the point image intervals (S201). The arithmetic part 210 reads a previously set predetermined interval from the memory 240, and compares it with the average point image interval detected from the first received light signals. In the case where the average point image interval is smaller than the previously set predetermined interval (S203), the arithmetic part 210 outputs a signal to the second driving part 260 to move the first light receiving part 23 in one direction, and returns to the processing of the step S201 (S205). In the case where the average point image interval is larger than the predetermined interval (S207), the arithmetic part 210 outputs a signal to the second driving part 260 to move the first light receiving part 23 in the + direction, and returns to the processing of the step S201 (S209). The second driving part 260 receives the signal from the arithmetic part 210, and in accordance with the inputted signal, it drives the second movement means 120. Besides, in the case where the average point image interval is the predetermined interval, the arithmetic part 210 proceeds to a processing of step S211. Incidentally, with respect to the comparison between the point image interval and the predetermined interval, a suitable value such as a minimum value, a maximum value, or a sum may be used in addition to the average of the respective point image intervals detected at the step S201. Besides, the arithmetic part 210 moves the condensing position of the light flux converted by the first conversion member by the second movement means to the minus side in the case where there is a region in which the point image interval is narrower than the predetermined interval range, and to the plus side in the case where there is a region in which the point image interval is wider than the predetermined interval range, and the point image interval can be adjusted within the predetermined interval range.

Next, the arithmetic part 210 reads the first received light signals from the first light receiving part 23, detects the respective point image levels on the basis of the read first received light signals, and obtains the average of the point image levels (S211). The arithmetic part 210 judges whether the average point image level is larger than the predetermined level read from the memory 240 (S213). Incidentally, with respect to the comparison between the point image level and the predetermined level, in addition to the average of the respective point image levels detected at the step S211, a suitable value such as a minimum value, a maximum value, or a sum may be used. In the case where the average point image level is smaller than the predetermined level, the arithmetic part 210 outputs a signal to the first driving part 250 to move the first illuminating optical system 10, and returns to the processing of the step S211 (S215). With respect to the movement direction of the first illuminating optical system 10, it is judged whether a point image level becomes large when the first illuminating optical system is moved in an arbitrary direction, and it may be moved in the direction in which the point image level becomes large. The first driving part 250 receives a signal from the arithmetic part 210, and in accordance with the inputted signal, it moves the first illuminating optical system 10 by the first movement means 110. In the case where the average point image level is larger than the predetermined level (S213), the arithmetic part 210 ends the independent mode automatic adjustment processing and proceeds to a processing of step S115.

On the other hand, again in the flowchart of FIG. 10, in the case of judgment of the manual adjustment (S109), the arithmetic part 210 performs the independent mode manual adjustment processing (S113). In the independent mode manual adjustment processing, the arithmetic part 210 receives the operation of the input part 270 by the operator, moves the first illuminating optical system 10 (projection side) and the first light receiving optical system 20 (light receiving side) independently, and enables the measurement in which a fine adjustment can be made. The operator uses the input part 270 to set projection side and light receiving side diopter values, and the first illuminating optical system 10 and the first light receiving optical system 20 are moved in accordance with the set diopter values.

FIG. 12 is a flowchart of the independent mode manual adjustment processing. Hereinafter, the independent mode manual adjustment processing of the step S113 will be described.

First, the arithmetic part 210 displays the diopter values adjusted in the interlock mode of the step S105 on the display part 230 (S301). Besides, the arithmetic part 210 captures the first received light signals concerning the Hartmann image from the first light receiving part 23, and displays the Hartmann image on the display part 230. The arithmetic part 210 captures the first received light signals from the first light receiving part 23 every predetermined period, and may update the display of the Hartmann image. Incidentally, the update of the display of the Hartmann image can be made at an arbitrary timing, not every period, for example, it may be made when the diopter value is changed by a manual operation.

Next, the arithmetic part 210 receives a projection side diopter value specifying signal from the projection side movement switch or the input part 270 such as the keyboard (S303). In the case where the diopter value specifying signal is not inputted or specified, the arithmetic part 210 proceeds to step S306. In the case of the input from the projection side movement switch, the arithmetic part 210 may change the diopter value by only a step value previously set for one input of the switch. In the case of the input from the keyboard, the arithmetic part 210 makes the inputted value the diopter value. The arithmetic part 210 displays the specified projection side diopter value on the display part 230, and outputs a drive instruction of the first movement means 110 to the first driving part 250 on the basis of the projection side diopter value (S305). Besides, the first driving part 250 receives the drive instruction from the arithmetic part 210, drives the first movement means 110 in accordance with the drive instruction, and moves the first illuminating optical system 10. The arithmetic part 210 judges whether the adjustment of the projection side diopter value is completed, and in the case of non-completion, it returns to the step S303, and in the case of completion, it proceeds to step S307 (S306). With respect to the judgment as to whether the adjustment is completed, for example, a signal of adjustment completion may be inputted from the input part 270.

Next, the arithmetic part 210 receives a light receiving side diopter value specifying signal from the light receiving side movement switch or the input part 270 such as the keyboard (S307). In the case where the diopter value specifying signal is not inputted or specified, the arithmetic part 210 proceeds to step S310. The specification of the diopter value by the light receiving side movement switch and the keyboard can be made the same as the case of the projection side. The arithmetic part 210 displays the specified light receiving side diopter value on the display part 230, and outputs a drive instruction of the second movement means 120 to the second driving part 260 on the basis of the light receiving side diopter value (S309). Besides, the second driving part 260 receives the drive instruction from the arithmetic part 210, and drives the second movement means 120 in accordance with the drive instruction to move the first light receiving optical system 20. By making the projection side and the light receiving side arbitrarily movable independently, an image suitable for analysis can be obtained for an ocular which is difficult to measure in the interlock mode. The arithmetic part 210 judges whether the adjustment of the light receiving side diopter value is completed, and returns to the step S307 in the case of non-completion, or proceeds to step S311 in the case of completion (S310). With respect to the judgment of completion of the adjustment, for example, an adjustment completion signal may be inputted from the input part 270.

The arithmetic part 210 uses the specified diopter value to judge whether measurement is started (S311). With respect to the judgment of the measurement start, for example, an instruction of an input as to whether measurement is started is displayed on the display part 230, and a signal of measurement start may be inputted from a measurement start button of the input part 270. In the case where it is judged that the measurement is started, the arithmetic part 210 ends the independent mode manual adjustment processing and proceeds to a processing of step 115. In the case where it is judged that the measurement is not started, the arithmetic part 210 returns to the processing of the step S303, and again sets a diopter value. Besides, a shift to the interlock mode or the automatic adjustment of the independent mode may be enabled by the mode changeover switch 271 or the operation changeover switch of the input part 270 at a suitable timing.

Returning to the flowchart of FIG. 10, the arithmetic part 210 detects signals under the measurement condition adjusted in the interlock mode or the independent mode (S115). The arithmetic part 210 captures the first received light signals concerning the Hartmann image by using the first light receiving part 23 of low noise CCDs or the like.

Besides, the arithmetic part 210 performs the Zernike analysis on the basis of the captured first received light signals and calculates the Zernike coefficients (S117). Next, the arithmetic part 210 performs an arithmetic processing of an optical characteristic on the basis of the first received light signals (S119). Here, the optical characteristic is an appropriate eye characteristic such as aberration or ocular refractive power. The arithmetic part 210 calculates the optical characteristic according to the measurement principle of the Hartmann wavefront sensor with respect to the first received light signals. The wavefront aberrations of an ocular optical system (ocular higher order aberrations) is obtained from the first received light signals. Further, the arithmetic part 210 displays the optical characteristic such as a measured Hartmann image or ocular higher order aberrations on the display part 230 (S121).

Besides, instead of the steps S115 to S121 or in parallel with those, the arithmetic part 210 captures second received light signals concerning an anterior eye image by the second light receiving part 35, and may calculate the optical characteristic such as wavefront aberrations (corneal higher order aberrations) occurring at the cornea, or corneal shape. After capturing the second received light signals, the arithmetic part 210 analyzes positions of ring images taken substantially concentrically with the bright point of corneal vertex reflection by using a method of image processing. With respect to the position of the ring, for example, approximately 256 points are acquired over 360 degrees on the circumference. The arithmetic part 210 calculates a tile of the cornea from the position of the ring. Besides, the arithmetic part 210 calculates the height of the cornea from the tilt of the cornea, and calculates the optical characteristic by treating the cornea similarly to an optical lens. The wavefront aberrations (corneal higher order aberrations) occurring at the cornea is obtained from the second received light signals. The arithmetic part 210 displays the calculated corneal higher order aberrations, the corneal shape and the like on the display part 230. Further, the arithmetic part 210 calculates a white light MTF, a Strehl ratio, a Landolt's ring pattern and the like, and may display them on the display part 230.

The arithmetic part 210 returns to the step S101 in the case where the measurement is continued, or ends the processing in the case where the measurement is not continued (S123).

5. MODIFIED EXAMPLES

Modified examples of the foregoing embodiment will be described below.

Modified Example of the Automatic Adjustment in the Independent Mode

Figure 15:
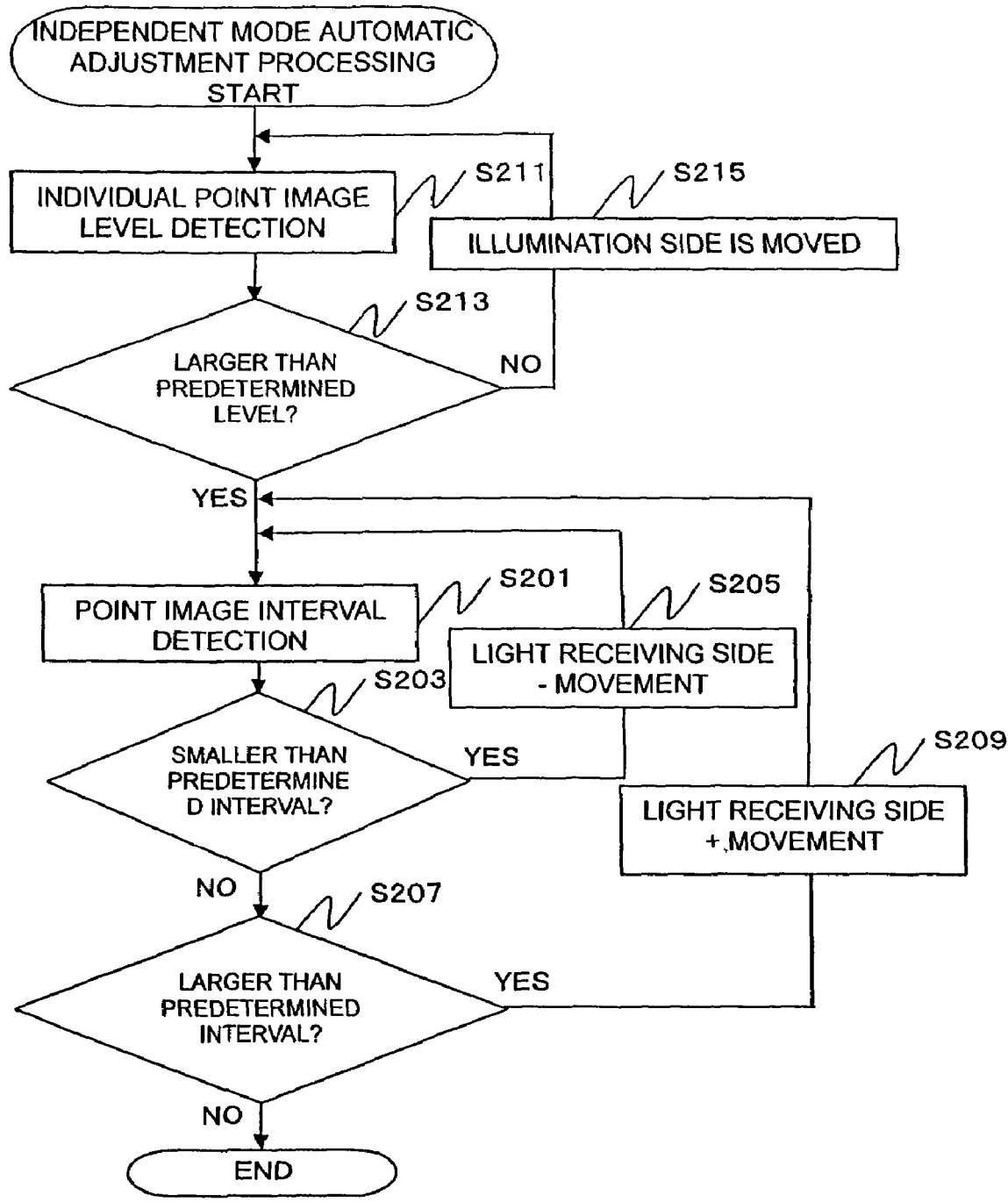
FIG. 15 is a first modified example of the independent mode automatic adjustment processing.

FIG. 15 shows a first modified example of the automatic adjustment processing in the independent mode of FIG. 11. In the automatic adjustment processing of the independent mode shown in FIG. 11, first, the point image intervals are adjusted in the steps S201 to S209, and the adjustment is performed in the steps S211 to S213 so that the point image levels come to have the predetermined value or more.

On the other hand, in the first modified example of the automatic adjustment processing of the independent mode shown in FIG. 15, contrary to one shown in FIG. 11, first, an adjustment is performed so that point image levels come to have a predetermined value or more, and next, an adjustment of point image intervals is performed. Although the sequence is changed as compared with the processing shown in FIG. 11, since the individual processing in the respective steps is not changed, the same reference signs as those of FIG. 11 are affixed and the detailed description will be omitted here.

Figure 16:
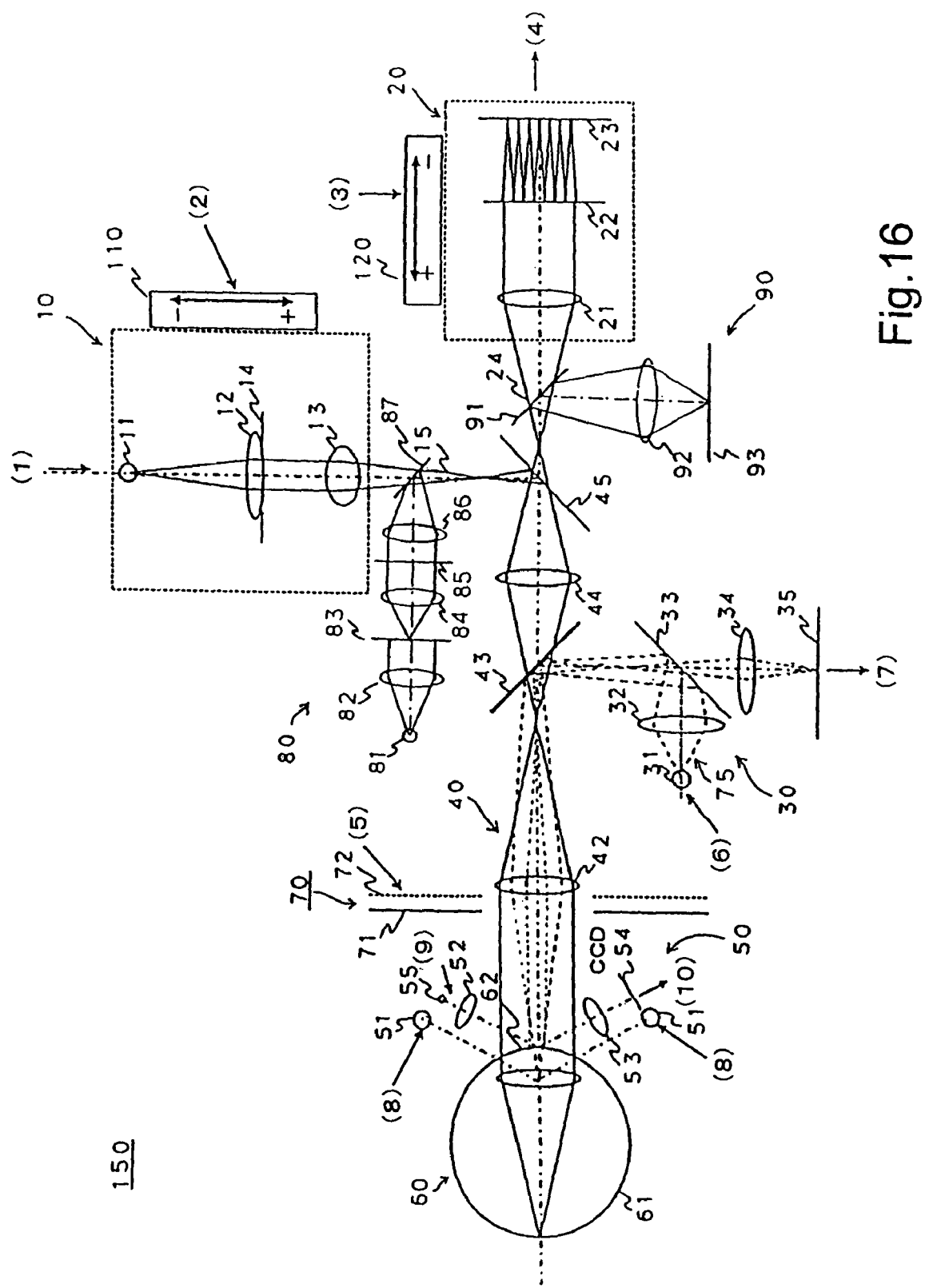
FIG. 16 is a view roughly sowing a modified example of an optical system of an ophthalmic measuring apparatus.

Modified Example of the Ophthalmic Measuring Apparatus Concerning the Embodiment FIG. 16 shows a modified example of the optical system of the ophthalmic measuring apparatus 100 shown in FIG. 1.

An ophthalmic measuring apparatus 150 shown in FIG. 16 includes an illuminating optical system 80 for refractive power measurement and a light receiving optical system 90 for refractive power measurement in addition to the ophthalmic measuring apparatus 100 shown in FIG. 1. At the refractive power measurement, both the optical systems function.

The illuminating optical system 80 for refractive power measurement includes a light source 81 for refractive power measurement, a collimate lens 82, a ring-like pattern 83 for refractive power measurement, a relay lens 84, and a beam splitter 87. An illumination light flux emitted from the light source 81 for refractive power measurement becomes a parallel light flux by the collimate lens 82, and illuminates the ring-shaped pattern 83 for refractive power measurement. A light flux from the illuminated ring-shaped pattern 83 for refractive power measurement becomes a parallel light flux by the relay lens 84, passes through a diaphragm 85 conjugate with a pupil and a relay lens 86, overlaps with an optical axis of a first illuminating optical system 10 through the beam splitter 87, and illuminates a retina 61 of a subject eye 60 through a common optical system 40. The ring-shaped pattern 83 for refractive power measurement is made to have a positional relation conjugate with the retina of the subject eye at the measurement of the orthoscopic subject eye.

The light receiving optical system 90 for refractive power measurement includes a beam splitter 91, a relay lens 92, and a light receiving part 93 for refractive power measurement. A reflected light flux from the retina 61 of the ring-illuminated subject eye 60 reaches the beam splitter 91 through the common optical system 40, is reflected here, and after being condensed by the relay lens 92, the light flux is received as a received light signal for refractive power measurement by the light receiving part 93 for refractive power measurement. The received light signal for refractive power measurement indicating the ring-shaped pattern image for refractive power measurement projected on the retina is sent to the arithmetic part 210.

The light receiving part 93 for refractive power measurement is preferably formed of a two-dimensional sensor. The arithmetic part 210 obtains the refractive power of the subject eye on the basis of the received light signal for refractive power measurement and from the ring-shaped pattern image for refractive power measurement projected on the retina. Since calculation for obtaining the refractive power of the subject eye is disclosed in Japanese Patent No. 2580215, the detail will be omitted here.

Whole Flowchart of a Modified Example

Figure 17:
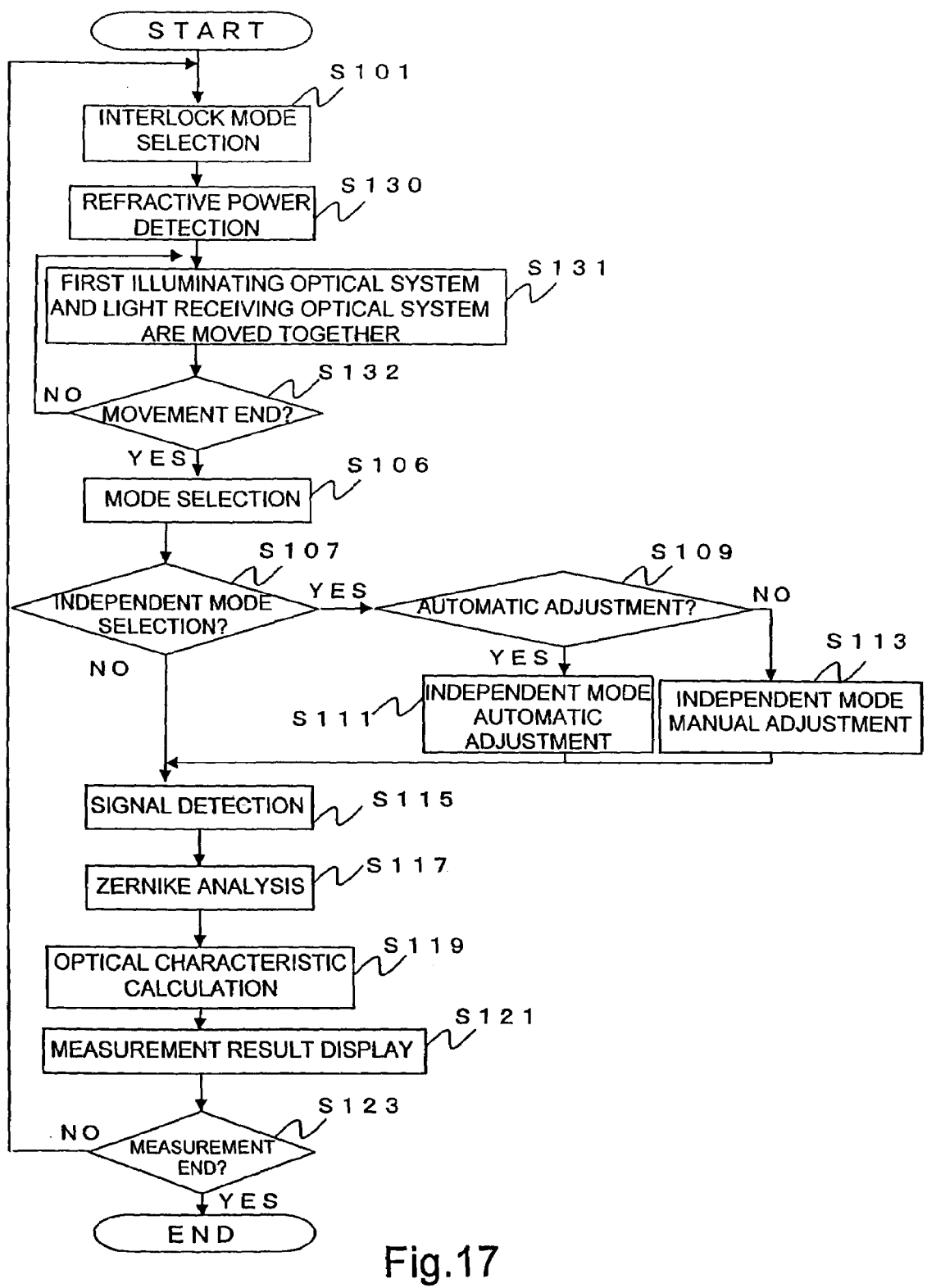
FIG. 17 is a view showing a first modified example of the whole flowchart of the ophthalmic measuring apparatus.

FIG. 17 shows a first modified example of the whole flowchart of the ophthalmic measuring apparatus of the embodiment. In the whole flowchart shown in FIG. 10, in the interlock mode, according to the level of the first received light signal of the first light receiving part, the interlock control of the first illuminating optical system 10 and first light receiving optical system 20 is performed in the steps S102, S103 and S105 shown in FIG. 10, and the rough position adjustment is performed. On the other hand, in the modified example shown in FIG. 17, refractive power measurement is performed in the interlock mode, and on the basis of the refractive power of the subject eye obtained by the measurement, the first illuminating optical system 10 and the first light receiving optical system 20 are moved together, which is a different point. Hereinafter, the different point will be described.

In the interlock mode of FIG. 17, on the basis of the received light signal for refractive power measurement, the arithmetic part 210 obtains the refractive power of the subject eye, and on the basis of the obtained refractive power, the interlock control of the first illuminating optical system 10 and the first light receiving optical system 20 is performed and the rough position adjustment is performed.

First, the arithmetic part 210 selects the interlock mode, and in parallel to that, it performs an alignment adjustment to the subject eye (S101). Next, the arithmetic part 210 illuminates the retina 61 of the subject eye 60 with the ring-shaped pattern 83 for refractive power measurement through the illuminating optical system 80 for refractive power measurement, receives the reflected light flux reflected from that by the light receiving part 93 for refractive power measurement, and obtains the refractive power of the subject eye 60 on the basis of the received light signal for refractive power measurement (S130). The arithmetic part 210 moves the first illuminating optical system 10 and the first light receiving optical system 20 together to positions corresponding to refractive power components of the obtained refractive power (S131). The arithmetic part 210 judges whether the movement adjustment is ended, and if not ended, it returns to the step S131, and if ended, it proceeds to step S106, and mode selection is performed (S132). With respect to the judgment of end of the movement adjustment, a suitable method, for example, the stop of the first illuminating optical system and the first light receiving optical system can be used. Besides, since the subsequent processing is the same as the flowchart shown in FIG. 10, the description will be omitted.

Second Modified Example of the Automatic Adjustment in the Independent Mode

Figure 18:
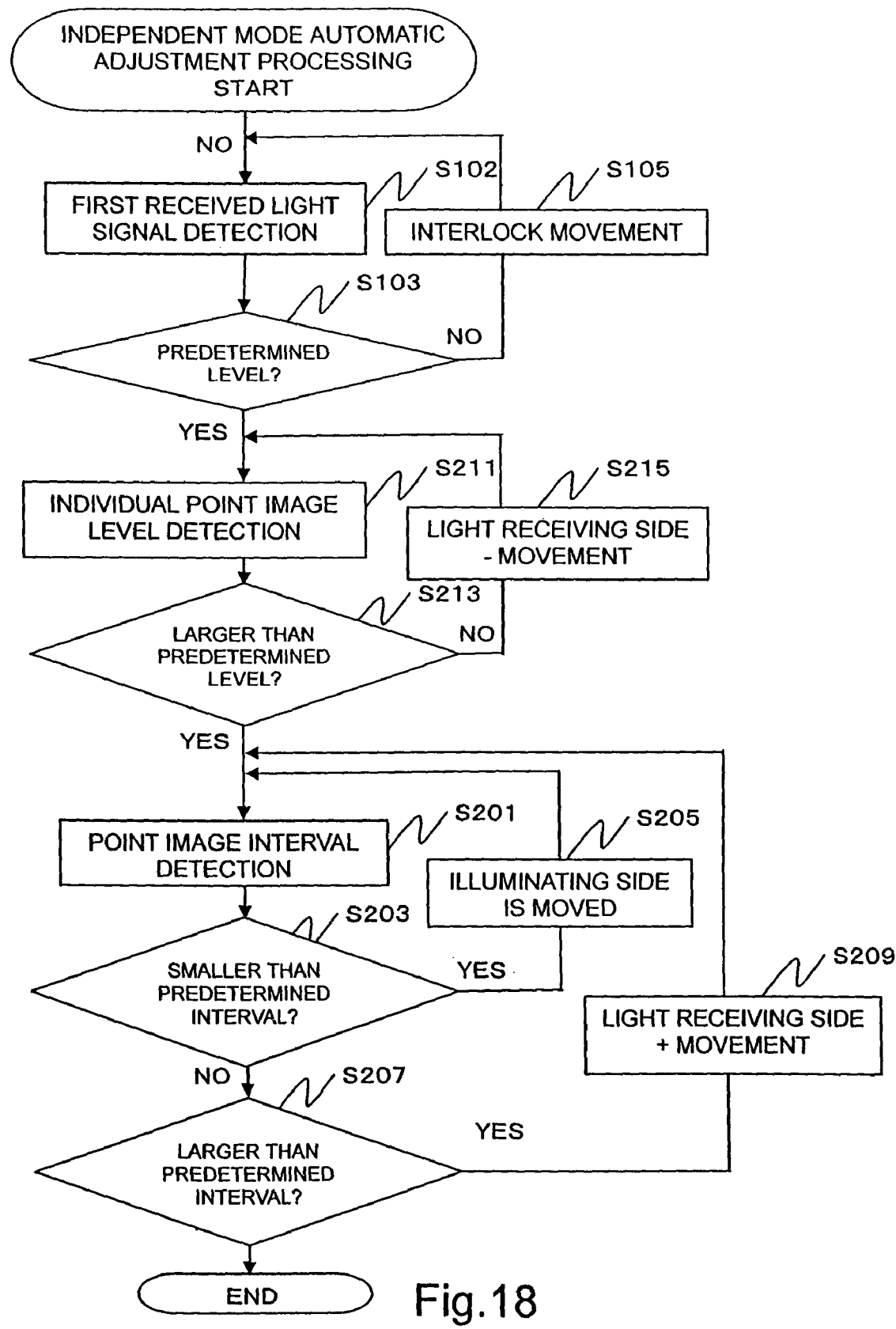
FIG. 18 is a view showing a second modified example of the independent mode automatic adjustment processing.

FIG. 18 shows a second modified example of the automatic adjustment processing of the independent mode. In the first modified example of the whole flowchart of the ophthalmic measuring apparatus in FIG. 17, when the automatic adjustment processing of the independent mode is selected (S107, S109), the second modified example of the automatic adjustment processing of the independent mode shown in FIG. 18 may be carried out.

In the automatic adjustment of the independent mode of this modified example, the arithmetic part 210 performs the interlock control of the first illuminating optical system 10 and the first light receiving optical system 20 on the basis of the level of the first received light signal, and then, performs a movement adjustment individually on the basis of the respective point image levels, and further, on the basis of the point image intervals, the individual movement adjustment is performed. The interlock control of the first illuminating optical system 10 and the fist light receiving optical system 20 on the basis of the level of the first received light signal is similar to the steps S102, S103 and S105 shown in FIG. 10, and the detailed description will be omitted by affixing the same reference signs. Next, the processing in which the individual movement adjustment is performed on the basis of the respective point image levels, and further, the individual movement adjustment is performed on the basis of the intervals of the point images, is similar to that shown in FIG. 11, and the detailed description will be omitted by affixing the same reference signs.

Third Modified Example of the Automatic Adjustment of the Independent Mode

Figure 19:
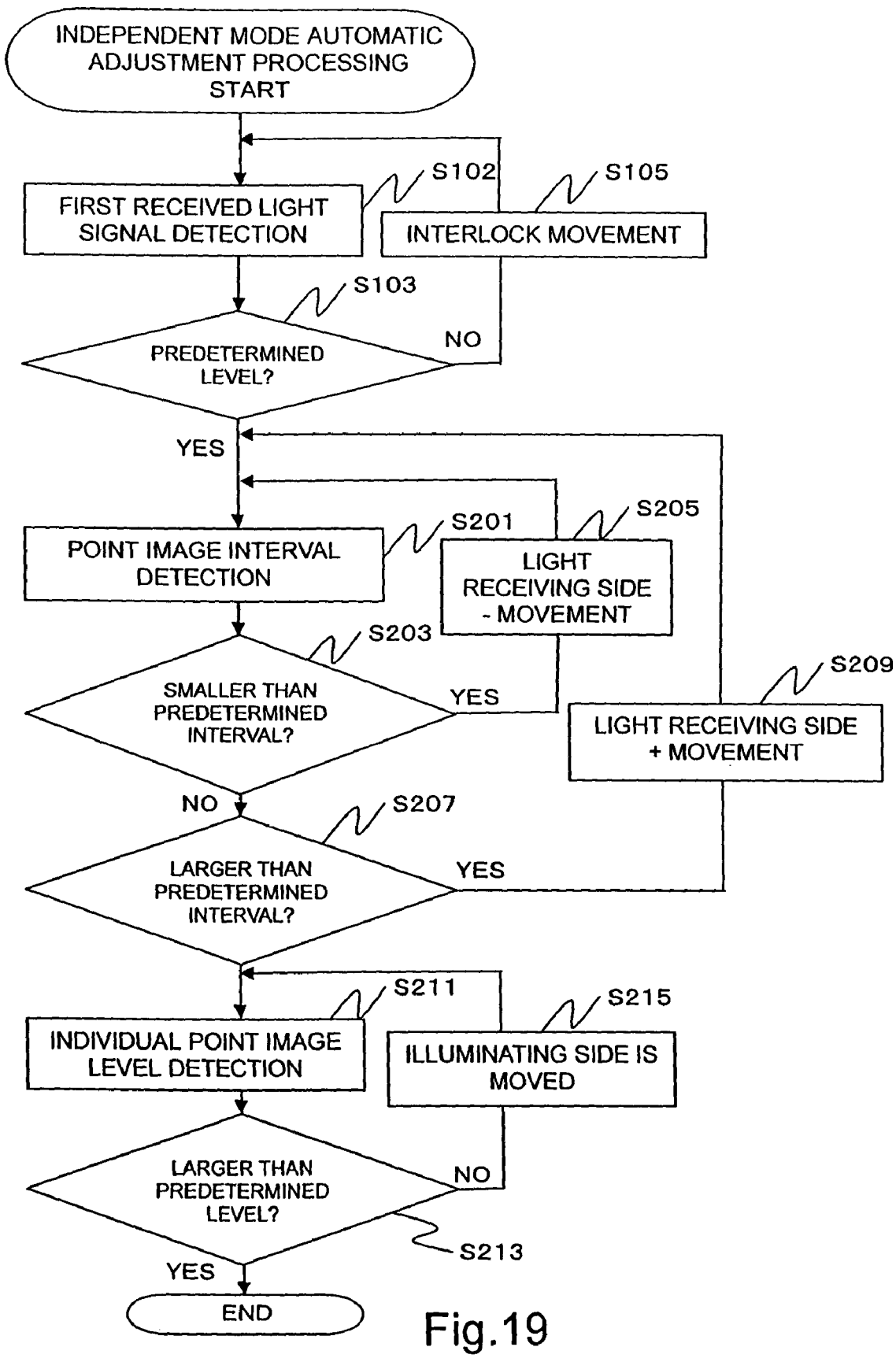
FIG. 19 is a view showing a third modified example of the independent mode automatic adjustment processing.

FIG. 19 shows a third modified example of the automatic adjustment processing of the independent mode. In the first modified example of the whole flowchart of the ophthalmic measuring apparatus in FIG. 17, when the automatic adjustment of the independent mode is selected (S107, S109), the third modified example of the automatic adjustment processing of the independent mode shown in FIG. 19 may be carried out.

In the automatic adjustment of the independent mode of this modified example, the interlock control of the first illuminating optical system 10 and the first light receiving optical system 20 is performed on the basis of the level of the first received light signal, and then, the movement adjustment is individually performed on the basis of the intervals of the point images, and further, the individual movement adjustment is performed on the basis of the respective point image levels. The interlock control of the first illuminating optical system 10 and the first light receiving optical system 20 on the basis of the levels of the first received light signals is similar to the steps S102, S103 and S105 shown in FIG. 10, and the detailed description will be omitted by affixing the same reference signs. Next, a processing in which the individual movement adjustment is performed on the basis of the intervals of the point images and the individual movement adjustment is performed on the basis of the respective point image levels, is similar to that shown in FIG. 15, and the detailed description will be omitted by affixing the same reference signs.

Figure 20:
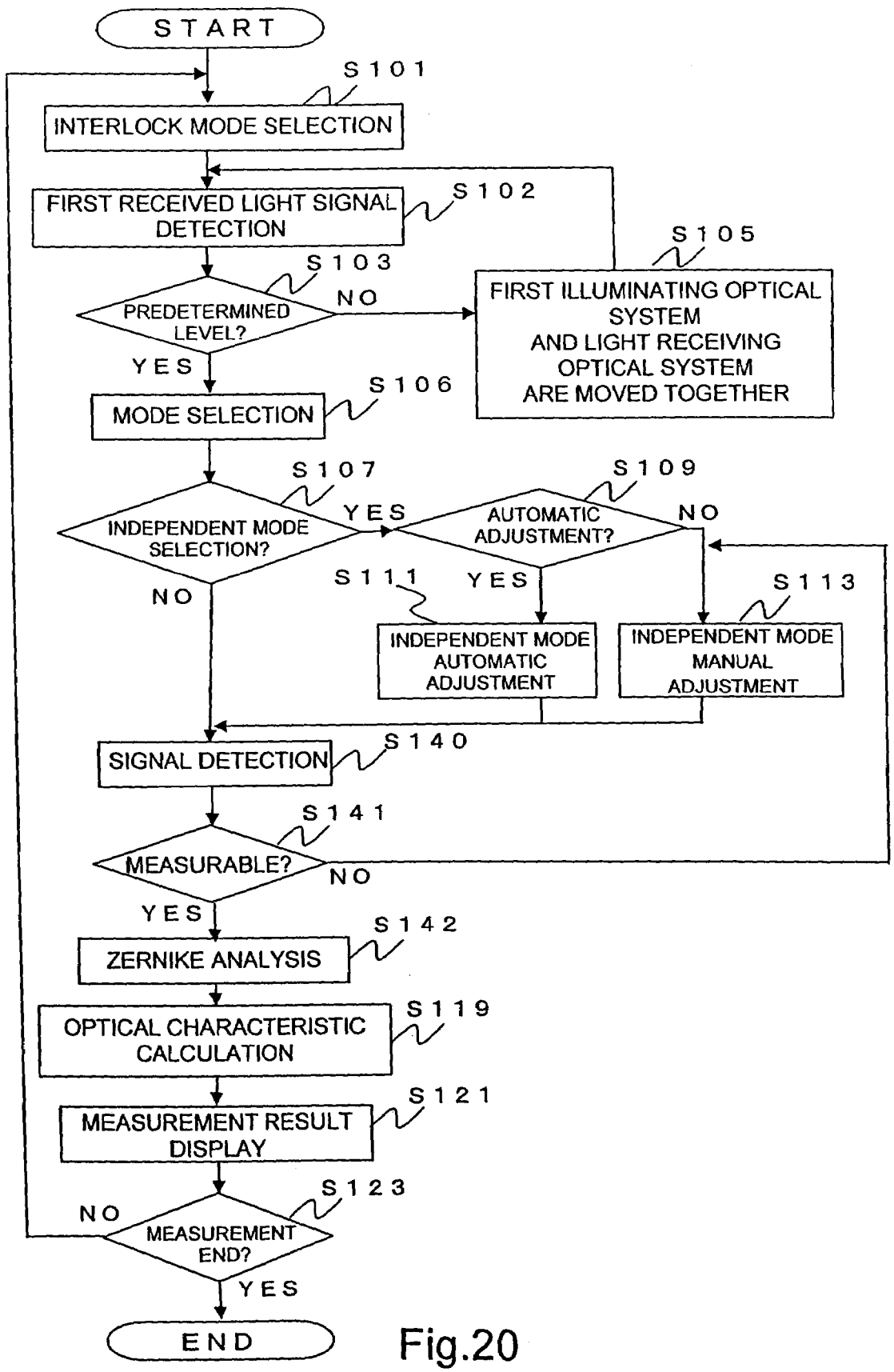
FIG. 20 is a second modified example of the whole flowchart of the ophthalmic measuring apparatus.

FIG. 20 shows a second modified example of the whole flowchart of the ophthalmic measuring apparatus of the embodiment. Especially, when the refractive index of a part of an eye is remarkably changed as in the case of initial axial cataract or as in the case where a refraction correcting operation is performed for an intense myopic eye, a case can occasionally occur in which even if the adjustment is performed in the independent mode, all the point images are not put into a measurable state. In the second modified example of the whole flowchart, at that time, plural Hartmann images at different diopter positions are detected, and those are combined to obtain the optical characteristic of the whole subject eye.

FIGS. 21A and 21B are views each showing a Hartmann image of an ocular in which refractive power of a part of an eye is different. The Hartmann images shown in FIGS. 21A and 21B indicate an example in which the vicinity of the center is substantially orthoscopic, and an intense myopic part remains in the peripheral portion. FIG. 21A shows a state in which an adjustment is performed in accordance with the refractive power in the vicinity of the center, and FIG. 21B shows a state in which an adjustment is performed in accordance with the refractive power of the peripheral portion. At the measurement, it becomes possible to measure the refractive power of the whole subject eye from the point images in the vicinity of the center of FIG. 21A and those in the peripheral portion of FIG. 21B.

In FIG. 20, since the processing from step S101 to S113 is similar to the processing in FIG. 10, the description will be omitted by affixing the same reference signs.

The arithmetic part 210 performs the signal detection in the adjusted state in each mode, and stores the detected first received light signals in the storage part (S140). The arithmetic part 210 judges whether the measurement can be sufficiently performed by use of the detected first received light signals (S141). The judgment as to whether the measurement can be performed can be made by, for example, whether a predetermined number of points of Hartmann images or more can be recognized, whether a predetermined number of points or more have a predetermined interval, or whether a predetermined number of points or more have a predetermined level or higher.

When judging that the first light received signals are insufficient for the measurement, the arithmetic part 210 returns to the step S113, performs the independent mode manual adjustment processing, and performs the adjustment so that point images of the insufficient area appear as clear ones having suitable intervals, and when the adjustment is ended, the arithmetic part proceeds to the signal detection processing of the step S140, detects Hartmann images under a different condition, and stores them in the storage part. The detection of the Hartmann images may be repeated plural times until a composite Hartmann image is formed and signals by which the measurement is enabled can be obtained. Next, the arithmetic part 210 forms the composite Hartmann image from the plural Hartmann images stored in the storage part, and performs the Zernike analysis (S142). The processing of forming the composite Hartmann image will be described below in detail.

A method will be described in which at a certain diopter position, when point images in some region of a Hartmann image are coupled or become blurred and can not be recognized, images there are acquired, and further, the position of the diopter is changed to a position where the region which could not be recognized before can be recognized, even if a region which could be recognized before can not be recognized, and images here are acquired and are combining with the previously acquired images to perform the analysis.

For example, after the Hartmann images are acquired for two screens, a barycentric position of point images at some diopter position (for example, the position of the center value of the diopter values of the two obtained screens) can be estimated from a barycentric position of point images detected from each of the Hartmann images. A movement amount of the point image is obtained from the images of the first light receiving part. The movement amount of an i-th point image is made $\Delta x_i$, $\Delta y_i$. This movement amount and the wavefront aberrations can be correlated by the following partial differential equation.

$$\frac{\partial W(X, Y)}{\partial X} = \frac{\Delta x}{f}$$ [Numerical Expression 5]

$$\frac{\partial W(X, Y)}{\partial Y} = \frac{\Delta y}{f}$$

Here, when the wavefront W is expressed by an expansion using a Zernike polynomial expression $Z_n^m$, the following is obtained.

$$W(X, Y) = \sum_{i=0}^{n} \sum_{j=0}^{i} c_i^{2j-i} Z_i^{2j-i}(X, Y)$$ [Numerical Expression 6]

By the change of the diopter position, at the wavefront W, only the Zernike coefficient $C_2^0$ corresponding to the diopter is changed. It is conceivable that the barycentric position of a point image is moved by an amount of only this change.

When a barycentric position of a point image at a diopter position before movement is $(X_{i1}, Y_{i1})$, a barycentric position of a point image at an estimated (analyzed) diopter position is $(X_i, Y_i)$, a movement amount is $\Delta X_{i1}, \Delta Y_{i1}$, a Zernike coefficient change amount is $\Delta(C_2^0)'$, and a distance between the Hartmann plate 22 and the first light receiving part 23 is F, the relation of the following expression is established.

$$X_i = \Delta X_{i1} + X_{i1} \qquad \text{[Numerical Expression 7]}$$
$$= \frac{\partial}{\partial X}\{\Delta(c_2^0)' Z_2^0(X_{i1}, Y_{i1})\} \cdot F + X_{i1}$$
$$= \Delta(c_2^0)' \frac{\partial}{\partial X} Z_2^0(X_{i1}, Y_{i1}) \cdot F + X_{i1}$$
$$Y_i = \Delta Y_{i1} + Y_{i1}$$
$$= \frac{\partial}{\partial Y}\{\Delta(c_2^0)' Z_2^0(X_{i1}, Y_{i1})\} \cdot F + Y_{i1}$$
$$= \Delta(c_2^0)' \frac{\partial}{\partial Y} Z_2^0(X_{i1}, Y_{i1}) \cdot F + Y_{i1}$$

Besides, an expression to calculate the Zernike coefficient $\Delta C_2^0$ from the diopter change amount $\Delta S_1$ is expressed by the following expression.

$$\Delta(C_2^0)' = -\frac{1}{4}\Delta S_1 \cdot r^2 \qquad \text{[Numerical Expression 8]}$$

Where, r is a pupil diameter (mm). Besides, the Zernike polynomial expression $Z_2^0$ is expressed by the following expression from FIG. 14.

$$Z_2^0 = 2X^2 + 2Y^2 - 1 \qquad \text{[Numerical Expression 9]}$$

Thus, when a barycentric position of a point image at a diopter value used for estimation and before the movement is made $(X_{i1a}, Y_{i1a})$, a barycentric position $(X_{ia}, Y_{ia})$ of a point image at a diopter position a to be estimated can be expressed by the following expression.

$$X_{ia} = -\frac{1}{4}\Delta S_1 \cdot r^2 \cdot 4 X_{i1a} \cdot F + X_{i1a} \qquad \text{[Numerical Expression 10]}$$
$$= -\Delta S_1 \cdot r^2 \cdot X_{i1a} \cdot F + X_{i1a}$$
$$Y_{ia} = -\frac{1}{4}\Delta S_1 \cdot r^2 \cdot 4 Y_{i1a} \cdot F + Y_{i1a}$$
$$= -\Delta S_1 \cdot r^2 \cdot Y_{i1a} \cdot F + Y_{i1a}$$

Further, when a barycentric position of a point image at a diopter position used for estimation and after the movement is made $(X_{i2b}, Y_{i2b})$, and a diopter change amount is $\Delta S_2$, a barycentric position $(X_{ib}, Y_{ib})$ of a point image at a diopter position b to be estimated (analyzed) is expressed by the following expression.

$$X_{ib} = -\frac{1}{4}\Delta S_2 \cdot r^2 \cdot 4 X_{i2b} \cdot F + X_{i2b} \qquad \text{[Numerical Expression 11]}$$
$$= -\Delta S_2 \cdot r^2 \cdot X_{i2b} \cdot F + X_{i2b}$$
$$Y_{ib} = -\frac{1}{4}\Delta S_2 \cdot r^2 \cdot 4 Y_{i2b} \cdot F + Y_{i2b}$$
$$= -\Delta S_2 \cdot r^2 \cdot Y_{i2b} \cdot F + Y_{i2b}$$

By calculating the wavefront W on the basis of the barycentric positions obtained by combining these, the result incorporating both the barycentric positions obtained for the two screens can be obtained. For example, in the case where i=1 to 100, points suitable for measurement at the position a are i=1 to 50, and points suitable for measurement at the position b are i=51 to 100, the barycentric position of the composite point image can be obtained by $$X_i = X_{1a} + X_{2a} \ldots + X_{50a} + X_{51b} + X_{52b} + \ldots X_{99b} + X_{100b}$$
$$Y_i = Y_{1a} + Y_{2a} \ldots + Y_{50a} + Y_{51b} + Y_{52b} + \ldots$$
$$Y_{99b} + Y_{100b} \qquad \text{[Numerical Expression 12]}$$

Incidentally, the combination of the Hartmann images is not limited to the two screens, and the same analysis can be performed from images more than those.

When the Zernike analysis is performed using this, the optical characteristic of the whole can be obtained. Thereafter, optical characteristic calculation is performed at step S119, and a measurement result is displayed at step 121. Since the processing at steps S119 to S123 is the same as the processing of the steps denoted by the same reference signs in the flowchart shown in FIG. 10, the description will be omitted.

According to the ophthalmic measuring apparatus of the invention, with respect to an eye which is difficult to measure, the adjustment to achieve the image suitable for analysis can be performed by the manual operation in the apparatus body, and the refractive wavefront measurement with high accuracy can be made.

This application claims priority from Japanese Patent Application 2002-236275, filed Aug. 14, 2002, which is incorporated herein by reference in their entirety.

What is claimed is:

1. An ophthalmic measuring apparatus comprising:
a first illuminating optical system including a first light source configured to emit a light flux of a first wavelength, for illuminating a retina of a subject eye, to be condensed on a place close to the retina, with the first illumination light flux from the first light source;
a first light receiving optical system including a first conversion member configured to convert a reflected light flux reflected by the retina of the subject eye into at least 17 light fluxes, and a first light receiving part configured to receive the plural light fluxes converted by the first conversion member as first received light signals, the first light receiving optical system configured to guide the reflected light flux to the first light receiving part;
first movement means for moving a condensing position of the first illuminating optical system;
second movement means for optically moving the first light receiving part and the first conversion member along an optical axis;
a mode changeover part configured to switch between an interlock mode in which movement operations of the first movement means and the second movement means are interlocked and an independent mode in which movement operations of the first movement means and the second movement means can be independently controlled, in which the first light receiving part and the first conversion member are moved by the second movement means along the optical axis independently of the movement operation of the first movement means; and
an arithmetic part configured to obtain an optical characteristic of the subject eye by performing a Zernike analysis on the basis of tilt angles of the light fluxes obtained by the first light receiving part, wherein the first movement means and the second movement means are configured to adjust the condensing position of the first illumination light flux and condensing positions of the light fluxes converted by the first conversion member according to received light positions and/or received light levels of the first received light signals at the first light receiving part, and when the independent mode is selected by the mode changeover part, the arithmetic part obtains received light position intervals from the first received light signals at the first light receiving part, and the condensing positions of the light fluxes converted by the first conversion member are configured to be adjusted by the second movement means, which moves the first light receiving part and the first conversion member on the basis of the obtained intervals independently of the first movement means, so that the obtained intervals fall within a predetermined interval range.

2. An ophthalmic measuring apparatus according to claim 1, wherein, when the independent mode is selected by the mode changeover part, the arithmetic part obtains the received light position intervals from the first received light signals at the first light receiving part, and the condensing positions of the light fluxes converted by the first conversion member are configured to be adjusted by the second movement means to a minus side in a case where there is a region in which the interval is narrower than the predetermined interval range, and to a plus side in a case where there is a region in which the interval is wider than the predetermined interval range.

3. An ophthalmic measuring apparatus according to claim 1, wherein, when the independent mode is selected by the mode changeover part, the arithmetic part further obtains received light levels from the first received light signals at the first light receiving part, and the condensing position of the first illumination light flux is configured to be adjusted by the first movement means moved independently of the second movement means on the basis of the obtained levels so that the obtained levels fall within a predetermined level range.

4. An ophthalmic measuring apparatus according to claim 1, wherein, when the independent mode is selected by the mode changeover part, in accordance with an operation of an input part by an operator, the condensing positions of the light fluxes converted by the first conversion member are configured to be adjusted by the second movement means, and the condensing position of the first illumination light flux can be adjusted by the first movement means.

5. An ophthalmic measuring apparatus comprising:
a first illuminating optical system including a first light source configured to emit a light flux of a first wavelength, for illuminating a retina of a subject eye, to be condensed on a place close to the retina, with the first illumination light flux from the first light source;
a first light receiving optical system including a first conversion member configured to convert a reflected light flux reflected by the retina of the subject eye into at least 17 light fluxes, and a first light receiving part configured to receive the plural light fluxes converted by the first conversion member, the first light receiving optical system configured to guide the reflected light flux to the first light receiving part;
first movement means for moving a condensing position of the first illuminating optical system;
second movement means for optically moving the first light receiving part and the first conversion member along an optical axis;
an arithmetic part configured to obtain an optical characteristic of the subject eye by combining tilt angle data of the light fluxes obtained by the first light receiving part under different conditions by the first movement means and the second movement means, and to perform a Zernike analysis on the basis of the combined data; and
a mode changeover part configured to switch between an interlock mode in which movement operations of the first movement means and the second movement means are interlocked, and an independent mode in which movement operations of the first movement means and the second movement means are independently controlled, in which the first light receiving part and the first conversion member are moved by the second movement means along the optical axis independently of the movement operation of the first movement means,
wherein
the arithmetic part configured to obtain the optical characteristic of the subject eye by combining the tilt angle data of the light fluxes obtained by the first light receiving part under different conditions in each of the interlock mode and the independent mode, and to perform the Zernike analysis on the basis of the combined data.

6. An ophthalmic measuring apparatus according to claim 1, wherein, when values based on the first received light signals are not greater than a predetermined level, the arithmetic part moves the first illuminating optical system and the first light receiving optical system together by the first and the second movement means.

7. An ophthalmic measuring apparatus according to claim 1, further comprising:
a refractive power measurement illuminating optical system configured to irradiate a retina of the subject eye with a pattern for refractive power measurement; and
a refractive power measurement light receiving optical system configured to receive a pattern image projected on the retina of the subject eye, wherein
the arithmetic part is configured to obtain refractive power from the pattern image received by the refractive power measurement light receiving optical system, and to move the first illuminating optical system and the first light receiving optical system together by the first and the second movement means on the basis of the refractive power.

8. An ophthalmic measuring apparatus according to claim 5, wherein, when values based on the first received light signals are not greater than a predetermined level, the arithmetic part moves the first illuminating optical system and the first light receiving optical system together by the first and the second movement means.

9. An ophthalmic measuring apparatus according to claim 5, further comprising:
a refractive power measurement illuminating optical system configured to irradiate a retina of the subject eye with a pattern for refractive power measurement; and
a refractive power measurement light receiving optical system configured to receive a pattern image projected on the retina of the subject eye, wherein
the arithmetic part is configured to obtain refractive power from the pattern image received by the refractive power measurement light receiving optical system, and to move the first illuminating optical system and the first light receiving optical system together by the first and the second movement means on the basis of the refractive power.

* * * * *